(12) United States Patent
Jacobs

(10) Patent No.: US 10,280,200 B2
(45) Date of Patent: May 7, 2019

(54) NON-NATURAL CONSENSUS ALBUMIN BINDING DOMAINS

(71) Applicant: Janssen Biotech, Inc., Horsham, PA (US)

(72) Inventor: Steven Jacobs, North Wales, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 15/710,385

(22) Filed: Sep. 20, 2017

(65) Prior Publication Data

US 2018/0009854 A1    Jan. 11, 2018

Related U.S. Application Data

(62) Division of application No. 14/842,218, filed on Sep. 1, 2015, now abandoned, which is a division of application No. 13/901,013, filed on May 23, 2013, now Pat. No. 9,156,887.

(60) Provisional application No. 61/651,642, filed on May 25, 2012, provisional application No. 61/776,918, filed on Mar. 12, 2013.

(51) Int. Cl.
| | |
|---|---|
| *C07K 14/00* | (2006.01) |
| *C07K 14/31* | (2006.01) |
| *C07K 14/47* | (2006.01) |
| *C07K 14/315* | (2006.01) |

(52) U.S. Cl.
CPC .......... *C07K 14/315* (2013.01); *C07K 14/001* (2013.01); *C07K 14/31* (2013.01); *C07K 14/47* (2013.01); *C07K 2319/01* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,856,456 | A | 1/1999 | Whitlow et al. |
| 6,162,903 | A | 12/2000 | Trowem et al. |
| 6,267,964 | B1 | 7/2001 | Nygren et al. |
| 6,521,427 | B1 | 2/2003 | Evans |
| 6,670,127 | B2 | 12/2003 | Evans |
| 7,635,749 | B2 | 12/2009 | Dennis et al. |
| 2004/0253247 | A1 | 12/2004 | Dennis et al. |
| 2005/0287153 | A1 | 12/2005 | Dennis |
| 2010/0216708 | A1 | 8/2010 | Jacobs et al. |
| 2010/0273979 | A1 | 10/2010 | Abrahmsen et al. |
| 2012/0100165 | A1 | 4/2012 | Arakawa et al. |

FOREIGN PATENT DOCUMENTS

| | | |
|---|---|---|
| WO | WO 2010/001908 A1 | 1/2010 |
| WO | WO 2010/093627 A2 | 8/2010 |
| WO | WO 2010/141329 A1 | 12/2010 |
| WO | WO 2011/130434 A2 | 10/2011 |
| WO | WO 2011/137319 A2 | 11/2011 |
| WO | WO 2014/081944 A2 | 5/2014 |

OTHER PUBLICATIONS

Alfthan, et al., "Properties of a single-chain antibody containing different linker peptides," Protein Engineering, 8(7): 735-731 (1995).
Andersen, et al., "Extending Half-life by Indirect Targeting of the Neonatal Fc Receptor (FCRn) Using a Minimal Albumin Binding Domain," The Journal of Biological Chemistry, 286(7): 5234-5241 (2011).
Breton, et al., "Prolonged Half-life in the circulation of a chemical conjugate between a pro-urokinase derivative and human serum albumin," European Journal of Biochemistry, 231: 563-569 (1995).
Coppieters, et al., "Formatted Anti-Tumor Necrosis Factor α VHH Proteins Derived From Camelids Show Superior Potency and Targeting to Inflamed Joints in a Murine Model of Collagen-Induced Arthritis," Arthritis & Rheumatism, 54(6): 1856-'866 (2006).
Cramer, et al., "Crystal structure of a bacterial albumin-binding domain at 1.4 Å resolution," FEBS Letters, 581: 3178-3182 (2007).
Dennis, et al., "Imaging Tumors with an Albumin-Binding Fab, a Novel Tumor-Targeting Agent," Cancer Research, 67(1): 254-261 (2007).
Dennis, et al., "Albumin Binding as a General Strategy for Improving the Pharmacokinetics of Proteins," The Journal of Biological Chemistry, 277(38): 35035-35043 (2002).
Flisiak, et al., "Albinterferon-alfa 2b: a new treatment option for hepatitis C," Expert Opinion in Biological Therapies, 10: 1509-1515 (2010).
Gaterc-Porekar, et al., "Obstacles and pitfalls in the PEGylation of therapeutic proteins," Current Opinion in Drug Discovery and Development, 11(2): 242-250 (2008).
Garrard, et al., "Selection of an anti-IGF-1 Fab from a Fab phage library created by mutagenesis of multiple CDR loops," Gene, 128: 102-109 (1993).
Goetsch, et al., "Identification of B- and T-Cell Epitopes of BB, a Carrier Protein Derived from the G Protein of *Streptococcus* Strain G148," Clinical and Diagnostic Laboratory Immunology, 125-132 (2003).
Hallewell, et al., "Genetically Engineered Polymers of Human CuZn Superoxide Dismutase," The Journal of Biological Chemistry, 264(9): 5260-5268 (1989).
He, et al., "An artificially evolved albumin binding module facilitates chemical shift epitope mapping of GA domain interactions with phylogenetically diverse albumins," Protein Science, 16: 1490-1494 (2007).
Hopp, et al., "The effects of affinity and valency of an albumin-binding domain (ABD) on the half-life of a single-chain diabody-ABD fusion protein," Protein Engineering, Design & Selection, 23(11): 827-834 (2010).

(Continued)

*Primary Examiner* — James H Alstrum-Acevedo
*Assistant Examiner* — Tara L Martinez
(74) *Attorney, Agent, or Firm* — Panitch Schwarze Belisario & Nadel LLP

(57) ABSTRACT

Non-natural albumin binding domains, polynucleotides encoding thereof and methods of making and using these domains and polynucleotides are useful in controlling the half-life of therapeutic molecules for patients.

8 Claims, 9 Drawing Sheets

Specification includes a Sequence Listing.

(56) References Cited

OTHER PUBLICATIONS

Johansson, et al., "Structure, Specificity, and Mode of Interaction for Bacterial Albumin-binding Modules," The Journal of Biological Chemistry, 277(10): 8114-8120 (2002).
Johansson, et al., "Solution Structure of the Albumin-binding GA Module: A Versatile Bacterial Protein Domain," Journal of Molecular Biology, 266: 859-865 (1997).
Johansson, et al, "The GA module, a mobile albumin-binding bacterial domain, adopts a three-helix-bindle structure," FEBS Letters, 374: 257-261 (1995).
Knappik, et al., "Fully Synthetic Human Combinatorial Antibody Libraries (HuCAL) Based on Modular consensus Frameworks and CDRs Randomized with Trinucleotides," Journal of Molecular Biology, 296: 57-86 (2000).
Roland E. Kontermann, "Strategies for extended serum half-life of protein therapeutics," Current Opinion in Biotechnology, 22: 868-876 (2011).
Kunkel, et al., "Rapid and Efficient Site-Specific Mutagenesis without Phenotypic Selection," Methods in Enzymology, 154: 367-382 (1987).
Kuo, et al., "Neonatal Fc Receptor: From Inmsunity to Therapeutics," Journal of Clinical Immunology, 30: 777-789 (2010).
Lehmann, et al., "Engineering proteins for thermostability: the use of sequence alignments versus rational design and directed evolution," Current Opinion in Biotechnology, 12: 371-375 (2001).
Lejon, et al., "Structural basis of the binding of naproxen to human serum albumin in the presence of fatty acids and the GA module," Acta Crystallographica, F64: 64-69 (2008).
Lejon, et al., "Crystal Structure and Biological Implications of a Bacterial Albumin Binding Module in Complex with Human Serum Albumin," The Journal of Biological Chemistry, 279(41): 42924-42928 (2004).
Libon, et al., "The serum albumin-binding region of streptococcal protein G (BB) potentiates the immunogenicity of the G130-230 RSV-A protein," Vaccine, 17: 406-414 (1999).
Makrides, et al., "Extended in Vivo Half-Life of Human Soluble Complement Receptor Type 1 Fused to a Serum Albumin-Binding Receptor," The Journal of Pharmacology and Experimental Therapeutics, 277(10): 534-542 (1996).
Metzner, et al., "Genetic fusion to albumin improves the pharmacokinetic properties of factor IX," Thrombosis Haemostasis Journal, 102: 634-644 (2009).
Müller, et al., "Improved Pharmacokinetics of Recombinant Bispecific Antibody Molecules by Fusion to Human Serum Albumin," The Journal of Biological Chemistry, 282(17): 1265012660 (2007).
Müller, et al., "Superior serum half life of albumin tagged TNF ligands," Biochemical and Biophysical Research Communications, 396: 793-799 (2010).
Nilvebrandt, "Engineering Bispecificity into a Single Albumin-Binding Domain," PLoS One, 6(10): e25791 (2011).
Northwestern University Glossary "Protein Scaffold," accessed Jan. 7, 2013.
Osborn, et al., "Albutropin: a growth hormone-albumin fusion with improved pharmacokinetics and pharmacodynamics in rats and monkeys," European Journal of Pharmacology, 456: 149-158 (2002).
Robinson, et al., "Covalent Attachment of Arc Repressor Subunits by a Peptide Linker Enhances Affinity for Operator DNA," Biochemistry, 35: 109-116 (1996).
Stefan Schulte, "Use of albumin fusion technology to prolong the half-life of recombinant factor VIIIa," Thrombosis Research, 122, Suppl. 4: S14-S19 (2008).
Sheffield, et al., "Prolonged in vivo anticoagulant activity of a hirudin-albumin fusion protein secreted from *Pichia pastoris*,".
Stähl, et al., "A dual expression system for the generation, analysis and purification of antibodies to a repeated sequence of the *Plasmodium falciparum* antigen Pf155/RESA," Journal of Immunological Methods, 124: 43-52 (1989).
Stork, et al., "A novel tri-functional antibody fusion protein with improved phannacokinetic properties generated by fusing a bispecific single-chain diabody with an albumin-binding domain from streptococcal protein G," Protein Engineering, Design & Selection, 20(11): 569-576 (2007).
Su, et al., "Effect of Chain length on the Formation and Stability of Synthetic α-Helical Coiled Coils," Biochemistry, 33: 15501-15510 (1994).
Tijink, et al., "Improved tumor targeting of anti-epidermal growth factor receptor Nanobodies through albumin binding: taking advantage of modular nanobody technology," Molecular Cancer Therapeutics, 7(8): 2288-2297 (2008).
Wunder, et al., "Albumin-Based Drug Delivery as Novel therapeutic Approach for Rheumatoid Arthritis," The Journal of Immunology, 170: 4793-4801 (2003).
Duttaroy, et al., "Development of a Long-Acting Insulin Analog Using Albumin Fusion Technology," Diabetes, 54: 251-258 (2005).
Holt, et al., "Anti-serum albumin domain antibodies for extending the half-lives of short lived drugs," Protein Engineering, Design & Selection, 21(5): 283-288 (2008).
Jonsson, et al., "Engineering of a femtomolar affinity binding protein to human serum albumin," Protein Engineering, Design & Selection, 21(8): 515-527 (2008).
Walker, et al., "Anti-serum albumin domain antibodies in the development of highly potent, efficarious and long-acting interferon," Protein Engineering, Design & Selection, 23(4): 271-278 (2010).
Sequence listing from WO201000329 (Lubman et al.).
Dai, et al., "The creation of a novel fluorescent protein by guided consensus engineering," Protein Engineering, Design & Selection, 20 (2): 69-79 (2007).
He, et al., "Structure, Dynamics, and Stability Variation in Bacterial Albumin Binding Modules: Implications for Species Specificity," Biochemistry, 45: 10102-10109 (2006).
Forrer, et al., "Consensus Design of Repeat Proteins," ChemBioChem, 5: 183-189 (2004).
Jacobs, et al., "Design of novel FN3 domains with high stability by a consensus sequence approach," Protein Engineering, Design & Selection 25 (3): 107-117 (2012).
Lehmann, et al., "From DNA sequence to improved functionality: using protein sequence comparisons to rapidly design a thermostable consensus phytase," Protein Engineering, 13 (1): 49-57 (2000).
Boris Steipe, "Consensus-Based Engineering of Protein Stability: From Intrabodies to Thermostable Enzymes," Methods Enzymology, 388: 176-186 (2004).
Johansson et al., "Differences in Backbone dynamics of two Homologous Bacterial Albumin-binding modules: Implcations for Binding Specificity and Bacterial Adaptation" J. Mol. Biol. vol. 316, pp. 1083-1099, 2002.
Stumpp et al., "Designing Repeat Proteins: Modular Leucine-rich Repeat Protein Libraries Based on Mammalian Ribonuclease Inhibitor Family" J. Mol. Biol. vol. 332, pp. 471-487, 2003.
Linhult et al., "Mutational Analysis of the Interaction Between Albumin-Binding Domain from Streptococcal Protein G and Human Serum Albumin", vol. 11, pp. 206-213, 2002.
Main et al. "Design of Stable a-Helical Arrays from an Idealized TPR motif", Structure, vol. 11, pp. 497-508, May 2003.

SEQUENCE LISTING

```
<160> NUMBER OF SEQ ID NOS: 55

<210> SEQ ID NO 1
<211> LENGTH: 44
<212> TYPE: PRT
<213> ORGANISM: Streptococcus sp. G148

<400> SEQUENCE: 1

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala
        35                  40

<210> SEQ ID NO 2
<211> LENGTH: 44
<212> TYPE: PRT
<213> ORGANISM: Streptococcus canis

<400> SEQUENCE: 2

Leu Ser Glu Ala Lys Glu Met Ala Ile Arg Glu Leu Asp Ala Gln Gly
1               5                   10                  15

Val Ser Asp Phe Tyr Lys Asn Lys Ile Asn Asn Ala Lys Thr Val Glu
            20                  25                  30

Gly Val Val Ala Leu Lys Asp Leu Ile Leu Asn Ser
        35                  40

<210> SEQ ID NO 3
<211> LENGTH: 42
<212> TYPE: PRT
<213> ORGANISM: Streptococcus canis

<400> SEQUENCE: 3

Leu Asp Gln Ala Lys Gln Ala Ala Leu Lys Glu Phe Asp Arg Tyr Gly
1               5                   10                  15

Val Ser Asn Tyr Tyr Lys Asn Leu Ile Asn Lys Ala Lys Thr Val Glu
            20                  25                  30

Gly Ile Met Glu Leu Gln Ala Gln Val Val
        35                  40

<210> SEQ ID NO 4
<211> LENGTH: 44
<212> TYPE: PRT
<213> ORGANISM: Artificial Sequence
```

```
<220> FEATURE:
<223> OTHER INFORMATION: Non-natural albumin binding domain

<400> SEQUENCE: 4

Leu Ala Gln Ala Lys Glu Ala Ala Ile Lys Glu Leu Lys Gln Tyr Gly
1               5                   10                  15

Ile Gly Asp Tyr Tyr Ile Lys Leu Ile Asn Asn Ala Lys Thr Val Glu
                20                  25                  30

Gly Val Glu Ser Leu Lys Asn Glu Ile Leu Lys Ala
            35                  40

<210> SEQ ID NO 5
<211> LENGTH: 44
<212> TYPE: PRT
<213> ORGANISM: Streptococcus equi

<400> SEQUENCE: 5

Leu Leu Lys Ala Lys Glu Ala Ala Ile Asn Glu Leu Lys Gln Tyr Gly
1               5                   10                  15

Ile Ser Asp Tyr Tyr Val Thr Leu Ile Asn Lys Ala Lys Thr Val Glu
                20                  25                  30

Gly Val Asn Ala Leu Lys Ala Glu Ile Leu Ser Ala
            35                  40

<210> SEQ ID NO 6
<211> LENGTH: 45
<212> TYPE: PRT
<213> ORGANISM: Finecoldia Magna

<400> SEQUENCE: 6

Leu Lys Asn Ala Lys Glu Asp Ala Ile Lys Glu Leu Lys Glu Ala Gly
1               5                   10                  15

Ile Lys Ser Gln Phe Phe Phe Asn Leu Ile Asn Asn Ala Lys Thr Val
                20                  25                  30

Glu Gly Val Glu Ser Leu Lys Asn Glu Ile Leu Lys Ala
            35                  40                  45

<210> SEQ ID NO 7
<211> LENGTH: 45
<212> TYPE: PRT
<213> ORGANISM: Finecoldia Magna

<400> SEQUENCE: 7

Leu Lys Asp Ala Lys Glu Lys Ala Ile Glu Ala Ile Arg Lys Glu Gly
1               5                   10                  15

Val Lys Ser Lys Leu Tyr Glu Asp Leu Ile Asn Lys Ala Lys Thr Ile
                20                  25                  30

Asp Gly Val Asn Ala Leu Arg Asp Gln Ile Ile Glu Ala
            35                  40                  45

<210> SEQ ID NO 8
<211> LENGTH: 45
<212> TYPE: PRT
<213> ORGANISM: Peptostreptococcus magnus

<400> SEQUENCE: 8

Leu Lys Asn Ala Lys Glu Glu Ala Ile Lys Glu Leu Lys Glu Ala Gly
1               5                   10                  15

Ile Thr Ser Asp Leu Tyr Phe Ser Leu Ile Asn Lys Ala Lys Thr Val
                20                  25                  30
```

Glu Gly Val Glu Ala Leu Lys Asn Glu Ile Leu Lys Ala
         35                  40                  45

<210> SEQ ID NO 9
<211> LENGTH: 45
<212> TYPE: PRT
<213> ORGANISM: Peptostreptococcus magnus

<400> SEQUENCE: 9

Leu Lys Asn Ala Lys Glu Ala Ala Ile Lys Glu Leu Lys Glu Ala Gly
1               5                   10                  15

Ile Thr Ala Glu Tyr Leu Phe Asn Leu Ile Asn Lys Ala Lys Thr Val
            20                  25                  30

Glu Gly Val Glu Ser Leu Lys Asn Glu Ile Leu Lys Ala
         35                  40                  45

<210> SEQ ID NO 10
<211> LENGTH: 45
<212> TYPE: PRT
<213> ORGANISM: Peptostreptococcus magnus

<400> SEQUENCE: 10

Leu Lys Asn Ala Lys Glu Asp Ala Ile Lys Glu Leu Lys Glu Ala Gly
1               5                   10                  15

Ile Ser Ser Asp Ile Tyr Phe Asp Ala Ile Asn Lys Ala Lys Thr Val
            20                  25                  30

Glu Gly Val Glu Ala Leu Lys Asn Glu Ile Leu Lys Ala
         35                  40                  45

<210> SEQ ID NO 11
<211> LENGTH: 45
<212> TYPE: PRT
<213> ORGANISM: Peptostreptococcus magnus

<400> SEQUENCE: 11

Leu Lys Asn Ala Lys Glu Asp Ala Ile Lys Glu Leu Lys Glu Ala Gly
1               5                   10                  15

Ile Thr Ser Asp Ile Tyr Phe Asp Ala Ile Asn Lys Ala Lys Thr Ile
            20                  25                  30

Glu Gly Val Glu Ala Leu Lys Asn Glu Ile Leu Lys Ala
         35                  40                  45

<210> SEQ ID NO 12
<211> LENGTH: 45
<212> TYPE: PRT
<213> ORGANISM: Finegoldia magna

<400> SEQUENCE: 12

Leu Ala Glu Ala Lys Lys Val Ala His Glu Glu Phe Thr Lys Ala Gly
1               5                   10                  15

Ile Thr Gly Lys Ile Phe His Asp Ala Ile Asp Ala Ala Lys Thr Val
            20                  25                  30

Glu Gly Leu Lys Ala Tyr Val Ala Glu Thr Leu Ala Ala
         35                  40                  45

<210> SEQ ID NO 13
<211> LENGTH: 45
<212> TYPE: PRT
<213> ORGANISM: Finegoldia magna

<400> SEQUENCE: 13

```
Leu Lys Glu Ala Lys Glu Lys Ala Val Glu Glu Leu Lys Glu Asn Gly
1               5                   10                  15

Ile Thr Ser Glu Lys Tyr Ile Asp Gln Ile Asn Lys Ala Lys Thr Val
            20                  25                  30

Glu Gly Val Asn Ala Leu Lys Asp Glu Ile Ile Lys Ala
        35                  40                  45

<210> SEQ ID NO 14
<211> LENGTH: 45
<212> TYPE: PRT
<213> ORGANISM: Finegoldia magnoa

<400> SEQUENCE: 14

Leu Lys Glu Ala Lys Glu Lys Ala Val Glu Glu Leu Lys Asn Asn Gly
1               5                   10                  15

Ile Thr Ser Glu Lys Tyr Ile Asp Gln Ile Asn Lys Ala Lys Thr Val
            20                  25                  30

Glu Gly Val Asn Ala Leu Lys Asp Glu Ile Ile Lys Ala
        35                  40                  45

<210> SEQ ID NO 15
<211> LENGTH: 45
<212> TYPE: PRT
<213> ORGANISM: Lactobacillus iners

<400> SEQUENCE: 15

Leu Ala Glu Ala Lys Lys Val Ala His Glu Glu Phe Thr Lys Ala Gly
1               5                   10                  15

Ile Thr Gly Lys Ile Phe His Asp Ala Ile Asp Ala Ala Lys Thr Val
            20                  25                  30

Glu Gly Leu Gln Ala Tyr Val Ala Glu Thr Leu Ala Ala
        35                  40                  45

<210> SEQ ID NO 16
<211> LENGTH: 45
<212> TYPE: PRT
<213> ORGANISM: Peptostreptococcus magnus

<400> SEQUENCE: 16

Leu Lys Asn Ala Lys Glu Asp Ala Ile Ala Glu Leu Lys Lys Ala Gly
1               5                   10                  15

Ile Thr Ser Asp Phe Tyr Phe Asn Ala Ile Asn Lys Ala Lys Thr Val
            20                  25                  30

Glu Glu Val Asn Ala Leu Lys Asn Glu Ile Leu Lys Ala
        35                  40                  45

<210> SEQ ID NO 17
<211> LENGTH: 45
<212> TYPE: PRT
<213> ORGANISM: Finegoldia magna

<400> SEQUENCE: 17

Leu Lys Glu Ala Lys Glu Lys Ala Val Glu Glu Leu Lys Asn Asn Gly
1               5                   10                  15

Ile Thr Ser Glu Lys Tyr Ile Glu Gln Ile Asn Lys Ala Lys Thr Val
            20                  25                  30

Glu Gly Val Asn Ala Leu Lys Asp Glu Ile Ile Lys Ala
        35                  40                  45

<210> SEQ ID NO 18
```

```
<211> LENGTH: 45
<212> TYPE: PRT
<213> ORGANISM: Lactobacillus iners

<400> SEQUENCE: 18

Leu Ala Glu Ala Lys Asn Val Ala His Ala Glu Phe Thr Lys Ala Gly
1               5                   10                  15

Ile Thr Gly Lys Ile Phe His Asp Ala Ile Asp Ala Ala Lys Thr Val
            20                  25                  30

Glu Gly Leu Gln Ala Tyr Val Ala Glu Thr Leu Ala Ala
        35                  40                  45

<210> SEQ ID NO 19
<211> LENGTH: 45
<212> TYPE: PRT
<213> ORGANISM: Lactobacillus iners

<400> SEQUENCE: 19

Leu Ala Glu Ala Lys Lys Ala Ala His Glu Glu Phe Thr Lys Ala Gly
1               5                   10                  15

Ile Thr Gly Lys Ile Phe His Asp Ala Ile Asp Ala Ala Lys Thr Val
            20                  25                  30

Glu Gly Leu Gln Ala Tyr Val Ala Glu Thr Leu Lys Ala
        35                  40                  45

<210> SEQ ID NO 20
<211> LENGTH: 45
<212> TYPE: PRT
<213> ORGANISM: Finegoldia magna

<400> SEQUENCE: 20

Leu Lys Glu Ala Lys Glu Lys Ala Ile Glu Glu Leu Lys Asn Asn Gly
1               5                   10                  15

Ile Thr Ser Glu Lys Tyr Ile Glu Gln Ile Asn Lys Ala Lys Thr Val
            20                  25                  30

Glu Gly Val Asn Ala Leu Lys Asp Glu Ile Ile Lys Ser
        35                  40                  45

<210> SEQ ID NO 21
<211> LENGTH: 45
<212> TYPE: PRT
<213> ORGANISM: Artificial Sequence
<220> FEATURE:
<223> OTHER INFORMATION: Non-natural albumin binding domain

<400> SEQUENCE: 21

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: Non-natural albumin binding domain
<220> FEATURE:
<221> NAME/KEY: MOD_RES
<222> LOCATION: (21)..(21)
<223> OTHER INFORMATION: Xaa1 may be any amino acid
```

```
<220> FEATURE:
<221> NAME/KEY: MOD_RES
<222> LOCATION: (22)..(22)
<223> OTHER INFORMATION: Xaa2 may be any amino acid
<220> FEATURE:
<221> NAME/KEY: MOD_RES
<222> LOCATION: (30)..(30)
<223> OTHER INFORMATION: Xaa3 may be any amino acid
<220> FEATURE:
<221> NAME/KEY: MOD_RES
<222> LOCATION: (31)..(31)
<223> OTHER INFORMATION: Xaa4 may be any amino acid
<220> FEATURE:
<221> NAME/KEY: MOD_RES
<222> LOCATION: (37)..(37)
<223> OTHER INFORMATION: Xaa5 may be any amino acid
<220> FEATURE:
<221> NAME/KEY: MOD_RES
<222> LOCATION: (41)..(41)
<223> OTHER INFORMATION: Xaa6 may be any amino acid

<400> SEQUENCE: 22

Leu Lys Glu Ala Lys Glu Lys Ala Ile Glu Glu Leu Lys Lys Ala Gly
1               5                   10                  15

Ile Thr Ser Asp Xaa Xaa Phe Asp Leu Ile Asn Lys Ala Xaa Xaa Val
                20                  25                  30

Glu Gly Val Asn Xaa Leu Lys Asp Xaa Ile Leu Lys Ala
            35                  40                  45

<210> SEQ ID NO 23
<211> LENGTH: 45
<212> TYPE: PRT
<213> ORGANISM: Artificial Sequence
<220> FEATURE:
<223> OTHER INFORMATION: Non-natural albumin binding domain
<220> FEATURE:
<221> NAME/KEY: MOD_RES
<222> LOCATION: (21)..(21)
<223> OTHER INFORMATION: Xaa1 is Lys, Arg, Asp, Glu, Ala, Gly, Phe or
     Tyr
<220> FEATURE:
<221> NAME/KEY: MOD_RES
<222> LOCATION: (22)..(22)
<223> OTHER INFORMATION: Xaa2 is Ala, Ser, Val, Lys, Arg, Asp, Glu or
     Tyr
<220> FEATURE:
<221> NAME/KEY: MOD_RES
<222> LOCATION: (30)..(30)
<223> OTHER INFORMATION: Xaa3 is Asp, Glu or Lys
<220> FEATURE:
<221> NAME/KEY: MOD_RES
<222> LOCATION: (31)..(31)
<223> OTHER INFORMATION: Xaa4 is Ala, Gly or Thr
<220> FEATURE:
<221> NAME/KEY: MOD_RES
<222> LOCATION: (37)..(37)
<223> OTHER INFORMATION: Xaa5 is  Val, Tyr or Ala
<220> FEATURE:
<221> NAME/KEY: MOD_RES
<222> LOCATION: (41)..(41)
<223> OTHER INFORMATION: Xaa6 is Qln, Asn, Lys, Arg or Glu

<400> SEQUENCE: 23

Leu Lys Glu Ala Lys Glu Lys Ala Ile Glu Glu Leu Lys Lys Ala Gly
1               5                   10                  15

Ile Thr Ser Asp Xaa Xaa Phe Asp Leu Ile Asn Lys Ala Xaa Xaa Val
                20                  25                  30

Glu Gly Val Asn Xaa Leu Lys Asp Xaa Ile Leu Lys Ala
            35                  40                  45

<210> SEQ ID NO 24
```

```
<211> LENGTH: 45
<212> TYPE: PRT
<213> ORGANISM: Artificial Sequence
<220> FEATURE:
<223> OTHER INFORMATION: Non-natural albumin binding domain
<220> FEATURE:
<221> NAME/KEY: MOD_RES
<222> LOCATION: (21)..(21)
<223> OTHER INFORMATION: Xaa1 is Lys, Ala or Tyr
<220> FEATURE:
<221> NAME/KEY: MOD_RES
<222> LOCATION: (22)..(22)
<223> OTHER INFORMATION: Xaa2 is Ala, Ser, Val or Tyr
<220> FEATURE:
<221> NAME/KEY: MOD_RES
<222> LOCATION: (30)..(30)
<223> OTHER INFORMATION: Xaa3 is Asp or Lys
<220> FEATURE:
<221> NAME/KEY: MOD_RES
<222> LOCATION: (31)..(31)
<223> OTHER INFORMATION: Xaa4 is Ala or Thr
<220> FEATURE:
<221> NAME/KEY: MOD_RES
<222> LOCATION: (37)..(37)
<223> OTHER INFORMATION: Xaa5 is Val, Tyr or Ala
<220> FEATURE:
<221> NAME/KEY: MOD_RES
<222> LOCATION: (41)..(41)
<223> OTHER INFORMATION: Xaa6 is Gln or Glu

<400> SEQUENCE: 24

Leu Lys Glu Ala Lys Glu Lys Ala Ile Glu Glu Leu Lys Lys Ala Gly
1               5                   10                  15

Ile Thr Ser Asp Xaa Xaa Phe Asp Leu Ile Asn Lys Ala Xaa Xaa Val
            20                  25                  30

Glu Gly Val Asn Xaa Leu Lys Asp Xaa Ile Leu Lys Ala
            35                  40                  45

<210> SEQ ID NO 25
<211> LENGTH: 45
<212> TYPE: PRT
<213> ORGANISM: Artificial Sequence
<220> FEATURE:
<223> OTHER INFORMATION: Non-natural albumin binding domain ABDCon2

<400> SEQUENCE: 25

Leu Lys Glu Ala Lys Glu Lys Ala Ile Glu Glu Leu Lys Lys Ala Gly
1               5                   10                  15

Ile Thr Ser Asp Ala Tyr Phe Asp Leu Ile Asn Lys Ala Lys Thr Val
            20                  25                  30

Glu Gly Val Asn Ala Leu Lys Asp Glu Ile Leu Lys Ala
            35                  40                  45

<210> SEQ ID NO 26
<211> LENGTH: 45
<212> TYPE: PRT
<213> ORGANISM: Artificial Sequence
<220> FEATURE:
<223> OTHER INFORMATION: Non-natural albumin binding domain ABDCon3

<400> SEQUENCE: 26

Leu Lys Glu Ala Lys Glu Lys Ala Ile Glu Glu Leu Lys Lys Ala Gly
1               5                   10                  15

Ile Thr Ser Asp Lys Tyr Phe Asp Leu Ile Asn Lys Ala Lys Thr Val
            20                  25                  30

Glu Gly Val Asn Ala Leu Lys Asp Glu Ile Leu Lys Ala
            35                  40                  45
```

-continued

<210> SEQ ID NO 27
<211> LENGTH: 45
<212> TYPE: PRT
<213> ORGANISM: Artificial Sequence
<220> FEATURE:
<223> OTHER INFORMATION: Non-natural albumin binding domain ABDCon4

<400> SEQUENCE: 27

Leu Lys Glu Ala Lys Glu Lys Ala Ile Glu Glu Leu Lys Lys Ala Gly
1               5                   10                  15

Ile Thr Ser Asp Tyr Ala Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 28
<211> LENGTH: 45
<212> TYPE: PRT
<213> ORGANISM: Artificial Sequence
<220> FEATURE:
<223> OTHER INFORMATION: Non-natural albumin binding domain ABDCon5

<400> SEQUENCE: 28

Leu Lys Glu Ala Lys Glu Lys Ala Ile Glu Glu Leu Lys Lys Ala Gly
1               5                   10                  15

Ile Thr Ser Asp Tyr Ser Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 29
<211> LENGTH: 45
<212> TYPE: PRT
<213> ORGANISM: Artificial Sequence
<220> FEATURE:
<223> OTHER INFORMATION: Non-natural albumin binding domain ABDCon6

<400> SEQUENCE: 29

Leu Lys Glu Ala Lys Glu Lys Ala Ile Glu Glu Leu Lys Lys Ala Gly
1               5                   10                  15

Ile Thr Ser Asp Tyr Val Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 30
<211> LENGTH: 45
<212> TYPE: PRT
<213> ORGANISM: Artificial Sequence
<220> FEATURE:
<223> OTHER INFORMATION: Non-natural albumin binding domain ABDCon7

<400> SEQUENCE: 30

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Gln Ile Leu Lys Ala
        35                  40                  45

<210> SEQ ID NO 31
<211> LENGTH: 45

```
<212> TYPE: PRT
<213> ORGANISM: Artificial Sequence
<220> FEATURE:
<223> OTHER INFORMATION: Non-natural albumin binding domain ABDCon8

<400> SEQUENCE: 31

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Asp Thr Val
            20                  25                  30

Glu Gly Val Asn Ala Leu Lys Asp Glu Ile Leu Lys Ala
        35                  40                  45

<210> SEQ ID NO 32
<211> LENGTH: 45
<212> TYPE: PRT
<213> ORGANISM: Artificial Sequence
<220> FEATURE:
<223> OTHER INFORMATION: Non-natural albumin binding domain ABDCon9

<400> SEQUENCE: 32

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Ala Val
            20                  25                  30

Glu Gly Val Asn Ala Leu Lys Asp Glu Ile Leu Lys Ala
        35                  40                  45

<210> SEQ ID NO 33
<211> LENGTH: 45
<212> TYPE: PRT
<213> ORGANISM: Artificial Sequence
<220> FEATURE:
<223> OTHER INFORMATION: Non-natural albumin binding domain ABDCon10

<400> SEQUENCE: 33

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Val Leu Lys Asp Glu Ile Leu Lys Ala
        35                  40                  45

<210> SEQ ID NO 34
<211> LENGTH: 45
<212> TYPE: PRT
<213> ORGANISM: Artificial Sequence
<220> FEATURE:
<223> OTHER INFORMATION: Non-natural albumin binding domain ABDCon11

<400> SEQUENCE: 34

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Tyr Leu Lys Asp Glu Ile Leu Lys Ala
        35                  40                  45

<210> SEQ ID NO 35
<211> LENGTH: 135
<212> TYPE: DNA
<213> ORGANISM: Artificial Sequence
<220> FEATURE:
```

<223> OTHER INFORMATION: Codon optimized cDNA for expressing non-natural albumin bindind domain ABDCon

<400> SEQUENCE: 35

```
ctgaaagaag cgaaagaaaa agcgattgaa gaactgaaaa aagcgggcat taccagcgat      60
tattattttg atctgattaa caaagcgaaa accgtggaag cgtgaacgc gctgaaagat      120
gaaattctga aagcg                                                       135
```

<210> SEQ ID NO 36
<211> LENGTH: 585
<212> TYPE: PRT
<213> ORGANISM: Homo sapiens

<400> SEQUENCE: 36

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320
```

```
Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
        340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 37
<211> LENGTH: 584
<212> TYPE: PRT
<213> ORGANISM: Macaca mulatta

<400> SEQUENCE: 37

Asp Thr His Lys Ser Glu Val Ala His Arg Phe Lys Asp Leu Gly Glu
1               5                   10                  15

Glu His Phe Lys Gly Leu Val Leu Val Ala Phe Ser Gln Tyr Leu Gln
            20                  25                  30

Gln Cys Pro Phe Glu His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

```
Pro Pro Leu Val Arg Pro Glu Val Asp Val Met Cys Thr Ala Phe His
        115                 120                 125

Asp Asn Glu Ala Thr Phe Leu Lys Lys Tyr Leu Tyr Glu Val Ala Arg
    130                 135                 140

Arg His Pro Tyr Phe Tyr Ala Pro Glu Leu Leu Phe Phe Ala Ala Arg
145                 150                 155                 160

Tyr Lys Ala Ala Phe Ala Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Asp
        195                 200                 205

Arg Ala Phe Lys Ala Trp Ala Val Ala Arg Leu Ser Gln Lys Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Met Cys Glu Asn Gln Asp Ser Ile Ser
        260                 265                 270

Ser Lys Leu Lys Glu Cys Cys Asp Lys Pro Leu Leu Glu Lys Ser His
    275                 280                 285

Cys Leu Ala Glu Val Glu Asn Asp Glu Met Pro Ala Asp Leu Pro Ser
290                 295                 300

Leu Ala Ala Asp Tyr Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Met Leu Leu Leu Arg Leu Ala Lys Ala
        340                 345                 350

Tyr Glu Ala Thr Leu Glu Lys Cys Cys Ala Ala Ala Asp Pro His Glu
    355                 360                 365

Cys Tyr Ala Lys Val Phe Asp Glu Phe Gln Pro Leu Val Glu Glu Pro
370                 375                 380

Gln Asn Leu Val Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ala Lys Cys Cys Lys Leu Pro Glu Ala Lys Arg Met Pro Cys
    435                 440                 445

Ala Glu Asp Tyr Leu Ser Val Val Leu Asn Arg Leu Cys Val Leu His
450                 455                 460

Glu Lys Thr Pro Val Ser Glu Lys Val Thr Lys Cys Cys Thr Glu Ser
465                 470                 475                 480

Leu Val Asn Arg Arg Pro Cys Phe Ser Ala Leu Glu Leu Asp Glu Ala
                485                 490                 495

Tyr Val Pro Lys Ala Phe Asn Ala Glu Thr Phe Thr Phe His Ala Asp
        500                 505                 510

Met Cys Thr Leu Ser Glu Lys Glu Lys Gln Val Lys Lys Gln Thr Ala
    515                 520                 525
```

```
Leu Val Glu Leu Val Lys His Lys Pro Lys Ala Thr Lys Glu Gln Leu
        530                 535                 540

Lys Gly Val Met Asp Asn Phe Ala Ala Phe Val Glu Lys Cys Cys Lys
545                 550                 555                 560

Ala Asp Asp Lys Glu Ala Cys Phe Ala Glu Glu Gly Pro Lys Phe Val
                565                 570                 575

Ala Ala Ser Gln Ala Ala Leu Ala
            580

<210> SEQ ID NO 38
<211> LENGTH: 584
<212> TYPE: PRT
<213> ORGANISM: Mus musculus

<400> SEQUENCE: 38

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320
```

```
Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
            340                 345                 350

Tyr Glu Ala Thr Leu Glu Lys Cys Cys Ala Glu Ala Asn Pro Pro Ala
                355                 360                 365

Cys Tyr Gly Thr Val Leu Ala Glu Phe Gln Pro Leu Val Glu Glu Pro
                370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
                420                 425                 430

Val Gly Thr Lys Cys Cys Thr Leu Pro Glu Asp Gln Arg Leu Pro Cys
                435                 440                 445

Val Glu Asp Tyr Leu Ser Ala Ile Leu Asn Arg Val Cys Leu Leu His
                450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
                500                 505                 510

Ile Cys Thr Leu Pro Glu Lys Glu Lys Gln Ile Lys Lys Gln Thr Ala
                515                 520                 525

Leu Ala Glu Leu Val Lys His Lys Pro Lys Ala Thr Ala Glu Gln Leu
                530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
                580

<210> SEQ ID NO 39
<211> LENGTH: 145
<212> TYPE: PRT
<213> ORGANISM: Artificial Sequence
<220> FEATURE:
<223> OTHER INFORMATION: Fusion protein Tencon25-ABDcon

<400> SEQUENCE: 39

Met Leu Pro Ala Pro Lys Asn Leu Val Val Ser Glu Val Thr Glu Asp
1               5                   10                  15

Ser Ala Arg Leu Ser Trp Thr Ala Pro Asp Ala Ala Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Lys Gly Gly His Arg
65                  70                  75                  80

Ser Asn Pro Leu Ser Ala Ile Phe Thr Thr Gly Gly Gly Gly Ser Gly
                85                  90                  95
```

```
Gly Gly Gly Ser Leu Lys Glu Ala Lys Glu Ala Ile Glu Glu Leu
            100                 105                 110

Lys Lys Ala Gly Ile Thr Ser Asp Tyr Tyr Phe Asp Leu Ile Asn Lys
            115                 120                 125

Ala Lys Thr Val Glu Gly Val Asn Ala Leu Lys Asp Glu Ile Leu Lys
            130                 135                 140

Ala
145

<210> SEQ ID NO 40
<211> LENGTH: 10
<212> TYPE: PRT
<213> ORGANISM: Artificial Sequence
<220> FEATURE:
<223> OTHER INFORMATION: Linker

<400> SEQUENCE: 40

Gly Gly Gly Gly Ser Gly Gly Gly Gly Ser
1               5                   10

<210> SEQ ID NO 41
<211> LENGTH: 145
<212> TYPE: PRT
<213> ORGANISM: Artificial sequence
<220> FEATURE:
<223> OTHER INFORMATION: Tencon-ABDCon fusion protein

<400> SEQUENCE: 41

Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Asn Leu
            35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Lys Gly Gly His Arg
65                  70                  75                  80

Ser Asn Pro Leu Ser Ala Glu Phe Thr Thr Gly Gly Gly Ser Gly
                85                  90                  95

Gly Gly Gly Ser Leu Lys Glu Ala Lys Glu Lys Ala Ile Glu Glu Leu
            100                 105                 110

Lys Lys Ala Gly Ile Thr Ser Asp Tyr Tyr Phe Asp Leu Ile Asn Lys
            115                 120                 125

Ala Lys Thr Val Glu Gly Val Asn Ala Leu Lys Asp Glu Ile Leu Lys
            130                 135                 140

Ala
145

<210> SEQ ID NO 42
<211> LENGTH: 6
<212> TYPE: PRT
<213> ORGANISM: Artificial sequence
<220> FEATURE:
<223> OTHER INFORMATION: N-terminal extension

<400> SEQUENCE: 42

Thr Ile Asp Gln Trp Leu
1               5
```

```
<210> SEQ ID NO 43
<211> LENGTH: 6
<212> TYPE: PRT
<213> ORGANISM: Artificial sequence
<220> FEATURE:
<223> OTHER INFORMATION: N-terminal extension

<400> SEQUENCE: 43

Thr Ile Asp Glu Trp Leu
1               5

<210> SEQ ID NO 44
<211> LENGTH: 51
<212> TYPE: PRT
<213> ORGANISM: Artificial sequence
<220> FEATURE:
<223> OTHER INFORMATION: ABDCon12

<400> SEQUENCE: 44

Thr Ile Asp Glu Trp Leu Leu Lys Glu Ala Lys Glu Lys Ala Ile Glu
1               5                   10                  15

Glu Leu Lys Lys Ala Gly Ile Thr Ser Asp Tyr Tyr Phe Asp Leu Ile
            20                  25                  30

Asn Lys Ala Lys Thr Val Glu Gly Val Asn Ala Leu Lys Asp Glu Ile
        35                  40                  45

Leu Lys Ala
    50

<210> SEQ ID NO 45
<211> LENGTH: 6
<212> TYPE: PRT
<213> ORGANISM: Artificial sequence
<220> FEATURE:
<223> OTHER INFORMATION: N-terminal extension

<400> SEQUENCE: 45

Ala Pro Ala Val Asp Val
1               5

<210> SEQ ID NO 46
<211> LENGTH: 6
<212> TYPE: PRT
<213> ORGANISM: Artificial sequence
<220> FEATURE:
<223> OTHER INFORMATION: N-terminal extension

<400> SEQUENCE: 46

Ile Ala Lys Glu Lys Ala
1               5

<210> SEQ ID NO 47
<211> LENGTH: 6
<212> TYPE: PRT
<213> ORGANISM: Artificial Sequence
<220> FEATURE:
<223> OTHER INFORMATION: N-terminal extension

<400> SEQUENCE: 47

Val Pro Ala Ala Asp Val
1               5

<210> SEQ ID NO 48
<211> LENGTH: 6
<212> TYPE: PRT
<213> ORGANISM: Artificial Sequence
```

<220> FEATURE:
<223> OTHER INFORMATION: N-terminal extension

<400> SEQUENCE: 48

Thr Val Lys Ser Ile Glu
1               5

<210> SEQ ID NO 49
<211> LENGTH: 6
<212> TYPE: PRT
<213> ORGANISM: Artificial Sequence
<220> FEATURE:
<223> OTHER INFORMATION: N-terminal extension

<400> SEQUENCE: 49

Thr Pro Ala Val Asp Ala
1               5

<210> SEQ ID NO 50
<211> LENGTH: 6
<212> TYPE: PRT
<213> ORGANISM: Artificial Sequence
<220> FEATURE:
<223> OTHER INFORMATION: N-terminal extension

<400> SEQUENCE: 50

Thr Leu Lys Ser Ile Lys
1               5

<210> SEQ ID NO 51
<211> LENGTH: 6
<212> TYPE: PRT
<213> ORGANISM: Artificial Sequence
<220> FEATURE:
<223> OTHER INFORMATION: N-terminal extension

<400> SEQUENCE: 51

Trp Glu Lys Ala Ala Ala
1               5

<210> SEQ ID NO 52
<211> LENGTH: 6
<212> TYPE: PRT
<213> ORGANISM: Artificial Sequence
<220> FEATURE:
<223> OTHER INFORMATION: N-terminal extension

<400> SEQUENCE: 52

Ala Val Asp Ala Asn Ser
1               5

<210> SEQ ID NO 53
<211> LENGTH: 6
<212> TYPE: PRT
<213> ORGANISM: Artificial Sequence
<220> FEATURE:
<223> OTHER INFORMATION: N-terminal extension

<400> SEQUENCE: 53

Gln Leu Ala Ala Glu Ala
1               5

<210> SEQ ID NO 54
<211> LENGTH: 6
<212> TYPE: PRT
<213> ORGANISM: Artificial Sequence
<220> FEATURE:

```
<223> OTHER INFORMATION: N-terminal extension

<400> SEQUENCE: 54

Ala Leu Lys Ala Ala Ala
1               5

<210> SEQ ID NO 55
<211> LENGTH: 6
<212> TYPE: PRT
<213> ORGANISM: Artificial Sequence
<220> FEATURE:
<223> OTHER INFORMATION: N-terminal extension

<400> SEQUENCE: 55

Glu Lys Leu Ala Ala Ala
1               5
```

NON-NATURAL CONSENSUS ALBUMIN BINDING DOMAINS

CROSS-REFERENCE TO RELATED APPLICATIONS

This application is a divisional of U.S. application Ser. No. 14/842,218, filed 1 Sep. 2015, which is a divisional of U.S. application Ser. No. 13/901,013, filed 23 May 2013, now U.S. Pat. No. 9,156,887, granted 13 Oct. 2015, which claims the benefit of U.S. Provisional Application Ser. Nos. 61/651,642, filed 25 May 2012 and 61/776,918, filed 12 Mar. 2013, the entire contents of which are incorporated herein by reference in their entireties.

FIELD OF THE INVENTION

The present invention relates to albumin binding domains and methods of making and using them. More particularly, the present invention is directed to a non-natural albumin binding domain consensus sequence and variants thereof as described herein.

BACKGROUND OF THE INVENTION

Rapid elimination of biotherapeutic molecules via renal clearance contributes to limited clinical effectiveness or more frequent dosing for the patient. Renal clearance due to glomerular filtration is most associated with smaller biotherapeutics, as the rates of kidney filtration are greatly reduced for molecules with a molecular weight of greater 50,000 daltons (Kontermann, Curr Opin Biotechnol 22:868-76, 2011). Several approved biotherapeutic drugs contain active portions that on their own fall below the filtration limit and are thus cleared quickly. To overcome this limitation, a number of technologies have been introduced to effectively increase the size of the therapeutic molecule to reduce kidney filtration and resulting half-life.

PEGylation (PEG) of therapeutics is an effective way to increase the hydrodynamic radius of the protein and reduce glomerular filtration. One or several PEG chains can be coupled to the protein most commonly through conjugation to free thiol or amine groups on the protein surface. PEGylated versions of Adenosine deaminase, L-Asparaginase, Interferon alpha-2b, G-CSF, Human Growth Hormone, Erythropoietin, Uricase, and an anti-TNFalpha antibody fragment have all been approved for human therapy (Kontermann, Curr Opin Biotechnol 22:868-76, 2011). Limitations of PEGylation include production of heterogeneous products and difficulty in controlling the number of PEG molecules attached to certain proteins. PEGylation introduces additional conjugation as well as purification steps to the production of therapeutic proteins, resulting in decreased yields and increased costs of goods. PEGylation may also lead to renal tubular vacuolization in animals and patients as PEG chains are non-degradable in the kidneys (Gaberc-Porekar et al., Curr Opin Drug Discov Devel 11:242-250, 2008).

Coupling a therapeutic to an antibody Fc region to generate Fc-fusion proteins can be used to increase the serum half-life of therapeutic molecules. Immunoglobulins may exhibit long half-lives on the order of several weeks in humans due to their large size and recycling through FcRn (Kuo et al., J Clin Immunol 30:777-789, 2010). TNF receptor 2, LFA-3, CTLA-4, IL-1R, and TPO-mimetic peptide molecules are all approved therapies produced as Fc-fusions (Kontermann, Curr Opin Biotechnol 22:868-76, 2011). Fc-fusion proteins are not ideal for all therapeutic classes for several reasons. The homodimeric nature of the Fc region results in the production of a dimeric therapeutic protein, possibly leading to cellular activation due to receptor clustering. Fc-fusions must also be made in mammalian expression systems which may be more costly than prokaryotic systems.

In addition to Fc, albumin exhibits a long half-life in vivo due to FcRn recycling. At a concentration of approximately 40 g/L, Human Serum Albumin (HSA) is the most abundant protein found in the blood. FcRn recycling leads to a long half-life of approximately 19 days in humans. Additionally, biodistribution studies suggest that albumin may distribute within the body to areas important for targeting disease, such as inflamed joints or tumors (Wunder et al., J Immunol 170:4793-4801, 2003). Thus, the serum half-life of a number of proteins has been increased by producing them as either C-terminal or N-terminal fusions to HSA. Successful fusions include interferon alpha (Flisiak and Flisiak, Expert Opin Biol Ther 10:1509-1515, 2010), human growth hormone (Osborn et al., Eur J Pharmacol 456:149-158, 2002), tumor necrosis factor (Muller et al., Biochem Biophys Res Commun 396:793-799, 2010), coagulation factor IX (Metzner et al., Thromb Haemost 102: 634-644, 2009), coagulation factor VIIa (Schulte, Thromb Res 122 Suppl 4: S14-19, 2008), insulin (Duttaroy et al., Diabetes 54:251-258, 2005), urokinase (Breton et al., Eur J Biochem 231: 563-569, 1995), hirudin (Sheffield et al., Blood Coagul Fibrinolysis 12:433-443, 2001), and bispecific antibody fragments (Muller et al, J Biol Chem 282:12650-12660, 2007). HSA fusion proteins may have long serum half-lives, however large scale production of these fusion proteins is limited predominantly to yeast expression systems. Additionally, the large size of HSA may lead to a loss in activity of the therapeutic due to steric hindrance.

Therapeutic proteins may also be produced as fusion proteins to peptides or proteins that bind to serum albumin in the blood stream to increase their half life. Such albumin binding peptides include cysteine-constrained peptides or antibody fragments to albumin. Expression of a Fab antibody fragment as a fusion to cysteine-constrained peptides significantly increased the serum half-life of the Fab (Dennis et al., J Biol Chem 277:35035-35043, 2002; US2004/0253247A1). Coupling cysteine-constrained peptide to an antibody fragment led to better peak tumor accumulation and more homogeneous tumor distribution compared to Fab and mAb molecules targeting the same antigen (Dennis et al., Cancer Res 67:254-261, 2007; US2005/0287153A1). Further, a number of antibody fragments that bind specifically to albumin have been coupled to therapeutic moieties to increase the half life of the therapeutic. A camelid $V_{HH}$ antibody fragment (Nanobodies®) that binds to HSA was fused to another Nanobody® that binds to TNF-alpha (Coppieters et al., Arthritis Rheum 54: 1856-1866, 2006) or anti-EGFR Nanobodies® (Tijink et al., Mol Cancer Ther 7:2288-2297, 2008). Anti-albumin domain antibodies (dAbs) have been generated that bind to albumin, and have been fused to, for example, interleukin-1 receptor (Holt et al., Protein Eng Des Sel 21:283-288, 2008) and interferon alpha 2b (Walker et al., Protein Eng Des Sel 23:271-278, 2010) to improve their half life.

A number of naturally occurring protein domains from bacteria are known to interact with albumin, presumably to help such bacteria distribute throughout the host organism. These are 3-helix bundle protein domains approximately 6 kDa in size which use one face of the 3-helix bundle to interact with serum albumin (Cramer et al., FEBS Lett 581:3178-3182, 2007; Lejon et al., Acta Crystallogr Sect F Struct Biol Cry st Commun 64:64-69, 2008; Johansson et al., FEBS Lett 374:257-261, 1995; Johansson et al., J Mol Biol 266:859-865, 1997; Johansson et al., J Biol Chem 277:8114-8120, 2002). One such albumin binding domain derived from streptococcal protein G (Jonsson et al., Protein Eng Des Sel 21:515-527, 2008), has been most widely used to extend the serum half-life of proteins. Fusion to this domain has been shown to increase the half-life of soluble complement receptor type 1 (Makrides et al., J Pharmacol Exp Ther 277:534-542, 1996), a bispecific antibody (Stork et al., Protein Eng Des Sel 20:569-576, 2007), CD4 (Nygren et al., Vaccines 91:363-368, 1991; U.S. Pat. No. 6,267,964B1), Pf155/RESA (Stahl et al., J Immunol Methods 124:43-52, 1989), G-CSF (Frejd, F. PEGS Europe, Oct. 5, 2010), and affibody molecules binding to a number of targets (Andersen et al., J Biol Chem 286:5234-5241, 2011) (Frejd, F. PEGS Europe, Oct. 5, 2010). However, antibody production against the domain has been reported in patients and thus the use of the molecule for therapeutic applications may be challenging (Goetsch et al., Clin Diagn Lab Immunol 10:125-132, 2003; Libon et al., Vaccine 17:406-414, 1999).

A number of protein domains or peptides that bind to albumin are capable of extending the serum half-life and producing a more beneficial biodistribution pattern of therapeutic proteins. In order to use these albumin binding domains in therapeutic applications, a number of biophysical requirements need to be fulfilled, such as high expression levels in a host, solubility and stability, and minimal immunogenicity. The albumin binding moiety should bind to serum albumin with an affinity that effectively balances serum half-life and biodistribution with activity of the therapeutic moiety when bound and not bound to albumin.

SUMMARY OF THE INVENTION

One aspect of the invention is a protein comprising an isolated, non-natural albumin binding domain having the amino acid sequence of SEQ ID NO:21. Another aspect of the invention is an isolated non-natural albumin binding domain comprising an amino acid sequence at least 85%, 86%, 87%, 88%, 89%, 90%, 91%, 92%, 93%, 94%, 95%, 96%, 97%, 98%, 99% or 100% identical to SEQ ID NO: 21.

Yet another aspect of the invention is an isolated non-natural albumin binding domain comprising an amino acid sequence of SEQ ID NO: 21 having substitutions at 1, 2, 3, 4, 5, and/or 6 residues, and, preferably, wherein the substitutions at 1, 2, 3, 4, 5, and/or 6 residues may occur at amino acid positions Y21, Y22, L25, K30, T31, E33, G34, A37, L38, E41, I42 and/or A45 of SEQ ID NO: 21 or at amino acid positions Y21, Y22, K30, T31, A37, and/or E41 of SEQ ID NO: 21.

A further aspect of the invention is an isolated non-natural albumin binding domain comprising an amino acid sequence: LKEAKEKAIEELKKAGITSDX$_1$X$_2$FDLI NKAX$_3$X$_4$VEGVNX$_5$LKDX$_6$ILKA (SEQ ID NO: 22); wherein X$_1$, X$_2$, X$_3$, X$_4$, X$_5$, and X$_6$ can be any amino acid or a subset of certain amino acids.

In a further aspect of the invention, the isolated non-natural albumin binding domain comprises an extension of 5 amino acids at its N-terminus.

Another aspect of the invention is a method of making a non-natural albumin binding domain of the invention comprising providing a polynucleotide encoding the non-natural albumin binding domain; expressing the polynucleotide in a host or in vitro; and recovering the non-natural albumin binding domain. Another aspect of the invention is an isolated polynucleotide encoding the albumin binding domains of the invention. Another aspect of the invention is an isolated polynucleotide comprising a polynucleotide of SEQ ID NO: 35.

Another aspect of the invention is an isolated vector comprising the isolated polynucleotide of the invention and a host cell comprising the isolated vector of the invention.

Another aspect of the invention is a fusion protein comprising an albumin binding protein of the invention and a bioactive agent.

Another aspect of the invention is a pharmaceutical composition comprising the fusion protein of the invention and at least one pharmaceutically acceptable carrier or diluent.

DETAILED DESCRIPTION OF THE INVENTION

Figure 1:
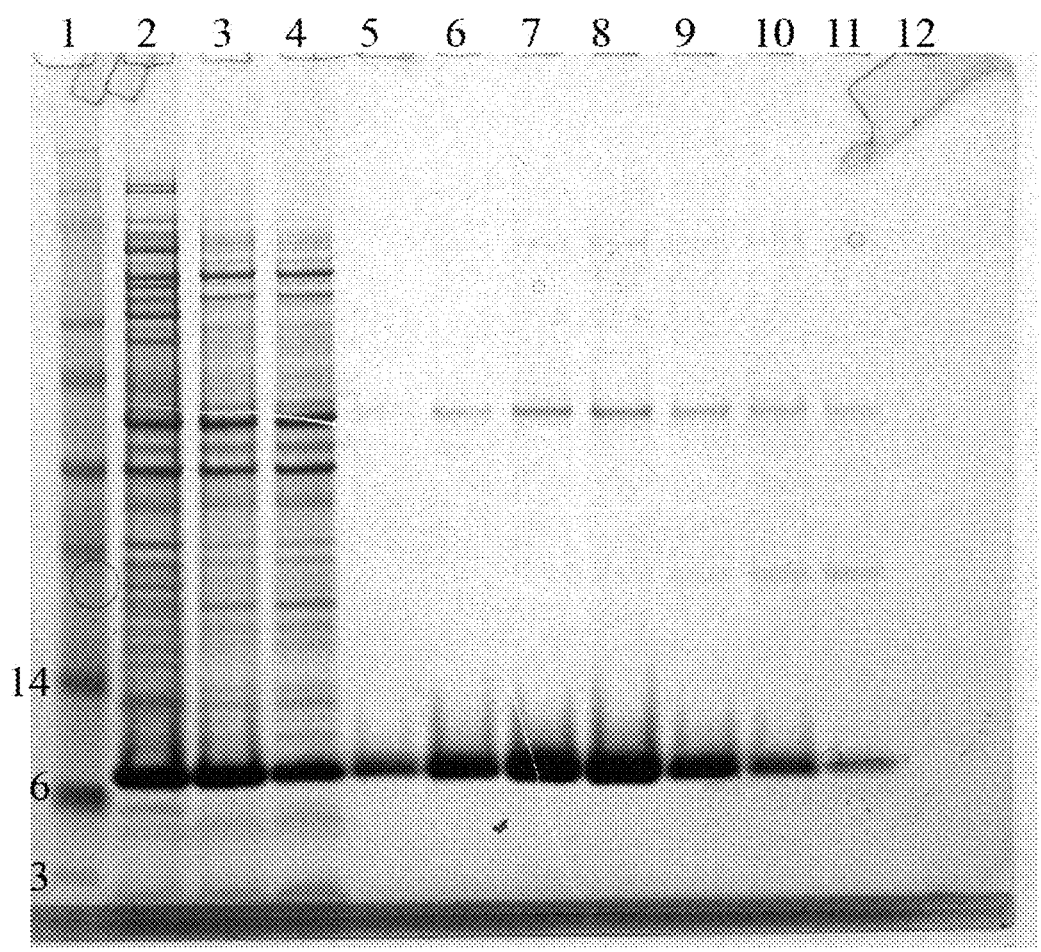
FIG. 1 shows SDS-PAGE analysis of purified ABDCon. Samples are as follows lane 1) SeeBlue plus 2 maker, 2) total cell lysate, 3) soluble cell lysate, 4) column flowthrough, 5-12) eluted fractions. Molecular weights of some of the marker bands are shown on the left.

The term "albumin binding domain" or "domain" as used herein refers to a polypeptide that binds albumin in vivo or in vitro. Albumin may be derived from any animal species, for example human, monkey, or rodent.

The term "$K_D$," as used herein, refers to the dissociation constant between albumin and the albumin binding domain.

The term "$K_{on}$," as used herein, refers to the on rate constant for association of an albumin binding domain to albumin to form an albumin binding domain/albumin complex.

The term "$K_{off}$," as used herein, refers to the off rate constant for dissociation of an albumin binding domain from the albumin binding domain/albumin complex.

The term "non-natural" as used herein refers to a domain that is synthetic, i.e., having an amino acid sequence not present in native polypeptides.

The term "substituting" or "substitutions" as used herein refers to altering, deleting or inserting, or to alterations, deletions or insertions of one or more amino acids or nucleotides in a polypeptide or polynucleotide sequence to generate a variant of that sequence.

The term "variant" as used herein refers to a polypeptide or a polynucleotide that differs from a reference polypeptide or a reference polynucleotide by one or more modifications, for example, substitutions, insertions or deletions.

The term "bioactive agent" as used herein refers to proteins, antibodies, peptides, nucleotides, small molecular pharmaceuticals and the like, that, when administered to an animal patient provides a benefit to that patient. Synthetically produced, naturally derived or recombinantly produced moieties are included in this term. Bioactive agents may be analogs, derivatives, agonists, antagonists, enantiomers or pharmaceutically acceptable salts of bioactive agents.

The term "stability" as used herein refers to the ability of a molecule to maintain a folded state under physiological conditions such that it retains at least one of its normal functional activities, for example, half life.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, bacteria, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "operably linked" as used herein refers to a positioning of components such that they function in their intended manner.

Amino acids are referred herein using their standard three or one letter codes:

Albumin Binding Domain Compositions

The present invention provides a synthetic albumin binding domain (ABDCon) (SEQ ID NO: 21) and variants thereof. ABDCon can be operably linked to a bioactive agent for enhancement of serum half-life and biodistribution of the therapeutic agent. ABDCon and variants thereof can be expressed at high levels in *E. coli*, are soluble, and have high thermal stability. The present invention provides polynucleotides encoding ADBCon and variants thereof, complementary nucleic acids, vectors, host cells, and methods of making and using them.

The present invention further provides synthetic albumin binding domain (ABDCon) that has an extension of 5 amino acid extension at the N-terminus. The extension improves stability of ABDCon.

The ABDCon binding domain was designed by calculating a consensus amino acid sequence of certain 3-helix bundle albumin binding domain (ABD) sequences deposited in the non-redundant protein database using ABD from *Streptococcus* sp. G148 protein G (SEQ ID NO: 1) as a template, and selecting the most prevalent amino acid at each sequence position (Table 6). ABDCon has a high affinity to human albumin with a $K_D$ of 75 pM and $K_{off}$ of $3.02 \times 10^{-5}$ 1/s when tested with conditions specified herein, and therefore bioactive agents operably linked to ABDCon may be largely bound to albumin once administered to an animal patient. In a human patient, molecules binding serum albumin too weakly will have short serum half-life due to renal filtering (Hopp et al., Protein Eng Des Sel 23:827-834, 2010), whereas molecules binding serum albumin too tightly will not be released from albumin at the preferred site of action, and thus in some cases may have reduced ability to modulate activity of the desired target and provide a therapeutic benefit. It is therefore one aspect of the invention to have and be able to generate ABDCon variants and binding domains having a spectrum of affinities to albumin and hence provide the ability to modulate the half life of the bioactive agent operably linked to ABDCon variants and binding domains.

One embodiment of the invention is an isolated non-natural albumin binding domain comprising an amino acid sequence at least 85%, 86%, 87%, 88%, 89%, 90%, 91%, 92%, 93%, 94%, 95%, 96%, 97%, 98%, 99% or 100% identical to SEQ ID NO: 21 (ABDCon): LKEAKEKA-IEELKKAGITSDYYFDLINKAKTVEGVNALKDEILKA.

Another embodiment of the invention is an isolated albumin binding domain comprising an amino acid sequence of SEQ ID NO: 21 having substitutions at 1, 2, 3, 4, 5, or 6, residues.

ABDCon variants can be designed by examining the crystal structure of an exemplary 3-helix bundle albumin binding protein in complex with albumin and making an assumption that ABDCon may bind albumin in a manner similar to the exemplary protein. An exemplary crystal structure that can be utilized is that of a GA module (protein G-related albumin-binding module) of protein PAB of an anaerobic bacterium Finegoldia magna (formerly Peptostreptococcus magnus) in complex with human albumin (Protein Data Base (PDB) code 1TF0 (Leion et al., J Biol Chem 279:42924-42928, 2004).

ABDCon variants having decreased affinity for albumin can be designed by various strategies, such as by disrupting predicted hydrophobic contacts, disrupting predicted pi-stacking between aromatic residues, introducing steric clashes by substitution with larger amino acids, disrupting salt bridges by removal of charged residues, and disrupting hydrogen bonding predicted to occur between ABDCon and albumin.

Introduced changes are designed to decrease binding affinity without changing the binding surface in a way that would abolish binding. For example, residue Y21 can be substituted for charged amino acids (Lys, Arg, Asp, Glu) or smaller amino acids (Ala, Gly) to reduce hydrophobic interactions between this residue and albumin residues V325 and F326. In addition, Y21 of ABDCon forms a hydrogen bond with the backbone of albumin residues N318 and D324 such that minor changes such as mutation to Phe may slightly weaken interactions. Residue Y22 of ABDCon is predicted to form hydrophobic as well as pi-stacking interactions with albumin residues F309 and F326. Therefore substitution of Y22 for smaller neutral amino acids Ala, Ser, Val or charged amino acids Lys, Arg, Asp, or Glu may decrease hydrophobic contacts and reduced affinity of the ABDCon variant to albumin. Residue K30 in ABDCon is predicted to form a salt-bridge with albumin residue E227 and thus K30 can be substituted for Asp or Glu to introduce repulsive charges and potentially reduce ABDCon affinity to albumin. Mutation to any non-charged amino acid may also reduce affinity by eliminating the salt-bridge. ABDCon residue T31 is predicted to form an intermolecular hydrogen bond with albumin residue N267 and substitutions for Ala or Gly can be used to disrupt the intermolecular hydrogen bond without introducing a large steric clash that might significantly destabilize the interaction. ABDCon residue A37 can be substituted for Val, Tyr, or other larger amino acid in order to introduce steric clashes. Residue E41 can be substituted for Gln or Asn to remove charge. Introduction of positively charged residues such as Lys or Arg can be expected to further reduce binding affinity. ABDCon residues L25, E33, G34, L38, I42, and A45 are predicted to form direct contact with albumin, and substitutions at these residues are likely to modulate ABDCon affinity to albumin Residue positions refer to ABDCon of SEQ ID NO: 21 and human albumin of SEQ ID NO: 36.

Alternatively, a random cocktail of amino acids can be used, utilizing for example NNK codons for substitutions at identified positions, and the resulting variants are measured for their binding to albumin using standard methods and methods described herein.

Exemplary ABDCon variants are variants having substitutions in at least one residue selected from Y21, Y22, L25, K30, T31, E33, G34, A37, L38, E41, I42 and A45 of SEQ ID NO: 21.

Exemplary ABDCon variants are variants having substitutions in at least one residue selected from Y21, Y22, K30, T31, A37 and E41 of SEQ ID NO: 21.

An exemplary ABDCon variant comprises an amino acid sequence LKEAKEKAIEELKKAGITSDX$_1$X$_2$FDLIN KAX$_3$X$_4$VEGVNX$_5$LKDX$_6$ILKA (SEQ ID NO: 22; wherein X$_1$, X$_2$, X$_3$, X$_4$, X$_5$, and X$_6$, can be any amino acid.

In other embodiments, an exemplary ABDCon variant comprises and amino acid sequence LKEAKEKAI EELKKAGITSDX$_1$X$_2$FDLINKAX$_3$X$_4$VEGVNX$_5$LKDX$_6$ ILKA (SEQ ID NO: 23), wherein
i) X$_1$ is Lysine (K), Arginine (R), Aspartate (D), Glutamate (E), Alanine (A), Glycine (G), Phenylalanine (F) or Tyrosine (Y);
ii) X$_2$ is Alanine (A), Serine (S), Valine(V), Lysine (K), Arginine (R), Aspartate (D), Glutamate (E) or Tyrosine (Y);
iii) X$_3$ is Aspartate (D), Glutamate (E) or Lysine (K);
iv) X$_4$ is Alanine (A), Glycine (G) or Threonine (T);
v) X$_5$ is Valine (V), Tyrosine (Y) or Alanine (A); and
vi) X$_6$ is Glutamine (Q), Asparagine (N), Lysine (K), Arginine (R) or Glutamate (E).

In other embodiments, an exemplary ABDCon variant comprises and amino acid sequence LKEAKEKAIEE LKKAGITSDX$_1$X$_2$FDLINKAX$_3$X$_4$VEGVNX$_5$LKDX$_6$IL KA (SEQ ID NO: 24), wherein
i) X$_1$ is Lysine (K), Alanine (A) or Tyrosine (Y);
ii) X$_2$ is Alanine (A), Serine (S), Valine(V) or Tyrosine (Y);
iii) X$_3$ is Aspartate (D) or Lysine (K);
iv) X$_4$ is Alanine (A) or Threonine (T);
v) X$_5$ is Valine (V), Tyrosine (Y) or Alanine (A); and
vi) X$_6$ is Glutamine (Q) or Glutamate (E).

Additional exemplary ABDCon variants comprise amino acid sequences shown in SEQ ID NOs: 25-34. ABDCon variants are tested for albumin binding using well known methods, for example in an in vitro assay using plasmon resonance (BIAcore, GE-Healthcare Uppsala, Sweden). The measured affinity of a particular ABDCon variant/albumin interaction can vary if measured under different conditions (e.g., osmolarity, pH). Thus, measurements of affinity and other binding parameters (e.g., $K_D$, $K_{on}$, $K_{off}$) are preferably made with standardized solutions of ABDCon variant and albumin, and a standardized buffer, such as the buffer described herein. Affinity of ABDCon variants to albumin may range from at least about $1 \times 10^{-5}$ M, at least about $1 \times 10^{-6}$ M, at least about $1 \times 10^{-7}$ M, at least about $1 \times 10^{-8}$ M, at least about $1 \times 10^{-9}$ M, at least about $1 \times 10^{-10}$ M, at least about $1 \times 10^{-11}$ M, at least about $1 \times 10^{-12}$ M, or at least about $1 \times 10^{-13}$ M. For example, various substitutions at Y22 of ABDCon (SEQ ID NO: 21) reduced affinity of the variants to albumin about 300-1,000 fold depending on a substitution (Table 4). Additional variants having substitutions at defined positions or at combinations of positions can be designed and generated by those skilled in the art and tested for a desired albumin binding affinity using routine methods.

ABDCon and variants thereof can further be modified by addition of a 5 amino acid extension to the N-terminus of ABDCon or ABDCon variant. The 5 amino acid extension may consist of an amino acid sequence TIDEWL (SEQ ID NO: 43), or any amino acid sequence shown in SEQ ID NOs: 42 or 45-55. Incorporating the N-terminal 5 amino acid extension into the ABDCon and variants thereof can increase the stability of the molecule. The N-terminal 5 amino acid extension may be structurally ordered as part of the first alpha helix of ABDCon and variants. The improved stability of the N-terminally extended molecules may therefore result from stabilizing the overall structure of the helix. The N-terminal ABDCon variants can be made using standard methods and their stability, for example thermal stability, assessed as described herein. Any albumin binding domain (ABD) may be modified with the addition of the 5 N-terminal amino acids to stabilize the ABD structure and improve stability, such as thermal stability of the resulting molecule.

ABDCon and variants thereof can be further modified at residues not affecting binding to albumin for the purpose of for example improving stability, reducing immunogenicity, improving solubility, or any other suitable characteristics. In one way to achieve this goal, the ABDCon and variants thereof can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, for example, residues that influence stability of the ABDCon domain. In this way, residues can be selected and combined from the parent and reference sequences so that the desired characteristics, such as improved stability is achieved. Alternatively, or in addition to the above procedures, other suitable methods of engineering can be used as known in the art.

Desirable physical properties of albumin binding domains of the invention include high thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol 12:371-375, 2001). High thermal stability may increase the yield of the expressed protein, improve solubility or activity, decrease immunogenicity, and minimize the need of a cold chain in manufacturing.

Residues that can be substituted to improve any characteristics of the albumin binding domains the invention can be determined by making the substitution and assaying for the desired characteristics of the albumin binding domain. For example, alanine scanning may be employed to identify positions in ABDCon and variants thereof that may affect the stability of the albumin binding domain.

In terms of loss of stability, i.e., "denaturing" or "denaturation" of a protein, is meant the process where some or all of the three-dimensional conformation imparting the functional properties of the protein has been lost with an attendant loss of activity and/or solubility. Forces disrupted during denaturation include intramolecular bonds, for example, electrostatic, hydrophobic, Van der Waals forces, hydrogen bonds, and disulfides. Protein denaturation can be caused by forces applied to the protein or a solution comprising the protein, such as mechanical force (for example, compressive or shear-force), thermal, osmotic stress, change in pH, electrical or magnetic fields, ionizing radiation, ultraviolet radiation and dehydration, and by chemical denaturants.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ($T_m$) temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

Chemical denaturation can likewise be measured by a variety of methods. Chemical denaturants include guanidinium hydrochloride, guanadinium thiocyanate, urea, acetone, organic solvents (DMF, benzene, acetonitrile), salts (ammonium sulfate lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The ABDCon binding domain and variants thereof may be operably linked to a bioactive agent. Exemplary bioactive agents are peptides and proteins that may be operably linked to ABDCon and variants thereof using well known linkers, for example a linker containing poly-glycine, glycine and serine (Gly-Ser linker), or alanine and proline. The use of naturally occurring as well as artificial peptide linkers is well known in the literature (Hallewell et al., J Biol Chem 264:5260-5268, 1989; Alfthan et al., Protein Eng. 8:725-731, 1995; Robinson & Sauer, Biochemistry 35:109-116, 1996; U.S. Pat. No. 5,856,456). The bioactive agent may be linked to the ABDCon or variant thereof from its C- or N-terminus. Multi-specific bioactive agents may also be linked to ABDCon. In these cases, ABDCon may be linked to the N-terminus or C-terminus of the molecule. ABDCon may also be positioned internally in such a multispecific agent such that it is linked to the C-terminus of one agent and the N-terminus of another. Bioactive agents may also be coupled to the albumin binding domains of the invention using chemical crosslinking well known in the art, for example using hydrazone or semicarbazone linkage. Exemplary bioactive agents are proteins specifically binding a target antigen such as proteins identified from fibronectin type III (FN3) repeat protein libraries, such as Tencon25-based libraries described in WO2011/137319A2 and WO2010/093627A2.

Additional moieties may be incorporated into ABDCon or variants thereof of the invention, such as toxin conjugates, polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the ABDCon coding sequences and may be generated by standard cloning and expression techniques. Alternatively, well known chemical coupling methods may be used to attach the moieties to recombinantly produced ABDCon of the invention.

ABDCon and variants thereof, as well as fusion proteins of bioactive agents and ABDCon can be assessed for their half life using well known pharmacokinetic properties in in vivo models. Exemplary ABDCon and variants thereof bind albumin with $K_D$ of about between 1 pM-1 µM, between 75 pM-860 nM, between 100 pM-500 nM, or between 1 nM-100 nM.

Generation and Production of ABDCon and Variants Thereof

Generation of the albumin binding domains of the invention is typically achieved at the nucleic acid level using standard methods. ABDCon variants having substituted codons at one or more specific residues can be synthesized for example using standard PCR cloning methods, or chemical gene synthesis according to methods described in U.S. Pat. No. 6,521,427 and U.S. Pat. No. 6,670,127, or using Kunkel mutagenesis (Kunkel et al., Methods Enzymol 154: 367-382, 1987). If randomized codons are to be used for any residue positions, randomization can be accomplished using well known methods, for example degenerate oligonucleotides matching the designed diversity, or for example using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues and simultaneously reducing the frequency of stop codons. The codon designations are according to the well known IUB code.

Synthesis of oligonucleotides with selected nucleotide "degeneracy" at certain positions is well known in that art, for example the TRIM approach (Knappek et al., J Mol Biol 296:57-86, 1999; Garrard & Henner, Gene 128:103-109, 1993). Such sets of nucleotides having certain codon sets can be synthesized using commercially available nucleotide or nucleoside reagents and apparatus.

Standard cloning and expression techniques are used to clone ABDCon or variants thereof into a vector or synthesize double stranded cDNA of ABDCon to express, or to translate the protein in vitro. Bioactive agents can be operably linked to ABDCon or variants thereof using well known methods.

Nucleic Acid Molecules and Vectors

The invention provides for nucleic acids encoding ABDCon or variants thereof of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions. Certain exemplary polynucleotides are disclosed herein, however, other polynucleotides which, given the degeneracy of the genetic code or codon preferences in a given expression system, encode ABDCon or variants thereof of the invention are also within the scope of the invention.

The polynucleotides of the invention may be produced by chemical synthesis, such as solid phase polynucleotide synthesis on an automated polynucleotide synthesizer and assembled into complete single or double stranded molecules. Alternatively, the polynucleotides of the invention may be produced by other techniques, such as a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, and the like. The polynucleotide sequences may also comprise additional sequences encoding additional amino acids that encode for example a marker or a tag sequence such as a hexa-histidine or an HA tag to facilitate purification or detection of the protein, a signal sequence, a fusion protein partner, such as cDNA encoding a bioactive agent, and the like.

An exemplary polynucleotide comprises sequences encoding ABDCon, sequences for a ribosome binding site, promoter sequence, terminator sequence, antibiotic resistance gene, and a bacterial origin of replication (ori). Exemplary polynucleotides encoding albumin binding domains of the invention are shown in SEQ ID NO: 35.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Host Cell Selection or Host Cell Engineering

ABDCon and variants thereof of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, NY (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, Hep G2, 653, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD(DE3), XL1-Blue, JM109, HMS174, HMS174 (DE3), and any of the natural or engineered *E. coli* spp, *Klebsiella* spp., or *Pseudomonas* spp strains.

Uses of Albumin Binding Domains of the Invention

The compositions of the non-natural albumin binding domain ABDCon and variants thereof of the invention can be used to modulate the half life and/or biodistribution of a bioactive agent within the tissue of an animal by operably linking ABDCon and the bioactive agent, and wherein the administration of the composition to an animal results in a half life and/or biodistribution of the bioactive agent which is different from the tissue distribution obtained upon administration of the active agent alone.

Pharmaceutical Compositions Comprising ABDCon or Variants Thereof

The ABDCon or variants thereof binding albumin operably linked to bioactive agents can be isolated using separation procedures well known in the art for capture, immobilization, partitioning, or sedimentation, and purified to the extent necessary for commercial applicability.

For therapeutic use, the bioactive molecule-ABDCon fusion proteins may be prepared as pharmaceutical compositions containing an effective amount of the bioactive agent-ABDCon fusion protein as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the bioactive agent-ABDCon fusion protein in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations are described, for example, in e.g. Remington: The Science and Practice of Pharmacy, 21$^{st}$ Edition, Troy, D. B. ed., Lippincott Williams and Wilkins, Philadelphia, Pa. 2006, Part 5, Pharmaceutical Manufacturing pp 691-1092, See especially pp. 958-989.

The mode of administration for therapeutic use of the bioactive agent-ABDCon fusion protein may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, suspension, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

While having described the invention in general terms, the embodiments of the invention will be further disclosed in the following examples that should not be construed as limiting the scope of the claims.

Example 1. Generation of Non-Natural Albumin Binding Domain

Design of Non-Natural Albumin Binding Domain Consensus (ABDCon)

A non-natural albumin binding domain (ABD) was designed by calculating a consensus amino acid sequence of 3-helix bundle ABD sequences deposited in the non-redundant protein database. In order to determine the consensus sequence, the ABD from *Streptococcus* sp. G148 protein G (SEQID NO: 1) was used as a template sequence for a BLAST search against the non-redundant NCBI protein database (http://blast_ncbi_nlm_nih_gov/Blast_cgi). All default settings were used for the BLAST search; Expect threshold=10, word size=3, matrix=BLOSUM62, gap costs=existence 11, extension 1, and compositional adjustments=conditional compositional score matrix adjustment. From this search, the 20 most closely related protein domains, listed in Table 1 (SEQ ID NOs: 1-20), were selected to be included in a multiple sequence alignment in order to determine a consensus. Only non-redundant sequences were selected. Several protein accession numbers are listed multiple times in Table 1, indicative that some proteins contain several closely related ABD domains SEQ ID NO:4 is a non-natural ABD derived by phage display and gene shuffling. (He et al., Protein Sci 16::1490-1494, 2007).

TABLE 1

| Protein Domain Accession Number | SEQ ID NO: |
|---|---|
| P19909 | 1 |
| AAA26847 | 2 |
| AAA26847 | 3 |
| 2FS1_A | 4 |
| YP_002123072 | 5 |
| ZP_07321229 | 6 |
| ZP_07321229 | 7 |
| AAA67503 | 8 |
| AAA67503 | 9 |
| AAA67503 | 10 |
| AAA67503 | 11 |
| ZP_07734934 | 12 |
| ZP_06946534 | 13 |
| ZP_07321240 | 14 |
| ZP_07906833 | 15 |
| Q51911 | 16 |
| YP_001692809 | 17 |
| ZP_07702676 | 18 |
| ZP_07702676 | 19 |
| ZP_07268895 | 20 |

A multiple sequence alignment was generated from the sequences listed using AlignX software (using all default settings). The sequence alignment shown in Table 6 was used to select the most prevalent amino acid at each sequence position to derive the albumin binding domain consensus sequence, ABDCon (SEQID NO: 21, Table 6). Tyr was chosen instead of Ile for position 21 as there was no clear consensus for this position and aromatic residues Tyr and Phe were well represented. Pairwise sequence identities between ABDCon range from 45% (SEQID NO: 3) to 82% (SEQID NOs: 8, 13, 14, and 16).

Gene Synthesis

The amino acid sequence of the albumin binding domain consensus (ABDCon) was back translated into a nucleic acid sequence encoding for ABDCon using preferred codons for *E. coli* expression as below (SEQID NO: 35) and a synthetic gene produced (BlueHeron Biotechnologies). 5' and 3' DNA sequences were added to the synthetic gene sequence of SEQID NO: 34 in order to add NdeI and XhoI sites for subcloning, as well as DNA sequences encoding for an N-terminal 8-His tag for protein purification. This gene was cloned into a pET26 vector (Novagen) for expression driven by a T7 promoter sequence and transformed into *E. coli* strain BL21(DE3) (Novagen).

Expression and Purification

Figure 2:
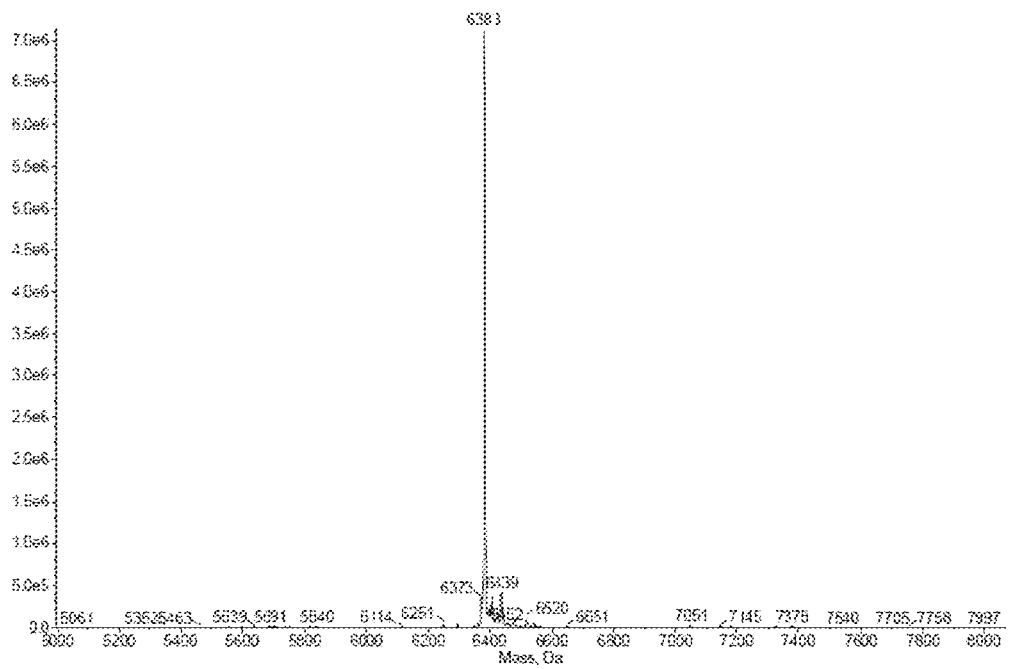
FIG. 2 shows electro-spray ionization mass spectrometry of purified ABDCon sample.
Figure 3:
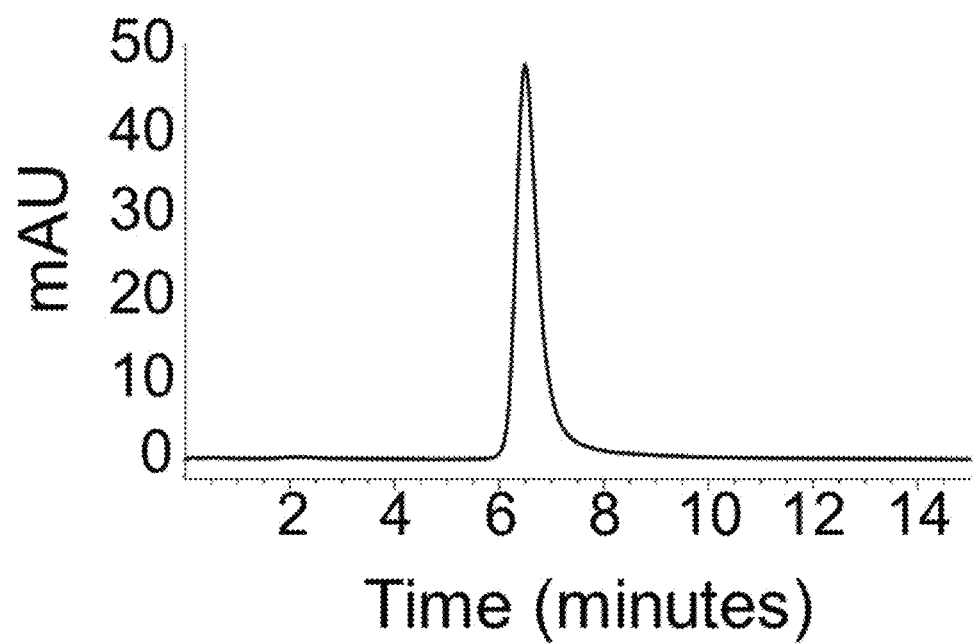
FIG. 3 shows size exclusion chromatography analysis of purified ABDcon as run in PBS.

For expression of ABDcon, 50 mL of LB media supplemented with 30 µg/mL kanamycin was inoculated with 1 colony and grown overnight at 37° C., 220 rpm shaking. The next day, 10 mL of the overnight culture was added to 100 mL of Terrific Broth supplemented with 30 µg/mL kanamycin and the culture grown at 37° C., 220 rpm for 2.5 hours. IPTG was added to a final concentration of 1 mM and the temperature reduced to 30° C. to induce protein expression. Cells were harvested 14 hours later by centrifugation at 4000×g for 20 minutes and the cell pellets stored at −20° C. Frozen cell pellets were resuspended in 5 mL of BugBuster HT (Novagen) per gram of wet pellet and gently mixed at room temperature for 30 minutes. The poly-histidine tagged ABDCon molecule was purified by Ni-NTA chromatography (GE Healthcare), eluting in a buffer of 50 mM sodium phosphate pH 7.4, 500 mM sodium chloride with a gradient of 10-250 mM imidazole. Fractions containing ABDCon were pooled and further purified by size exclusion chromatography using a Superdex75 16/60 column (GE Healthcare) with a mobile phase of PBS. Purity was assessed by SDS- PAGE analysis (FIG. 1). Mass spectrometry determined the mass to be 6383 Da, in agreement with the theoretical mass of 6382 Da (FIG. 2). Analytical size exclusion chromatography using a Superdex 75 5/150 column (GE Healthcare) shows that the ABDCon preparation is free of aggregates and elutes at a time consistent with a monomeric protein (FIG. 3).

Example 2. Characterization of ABDCon

Thermal Stability of ABDCon

Figure 4A:
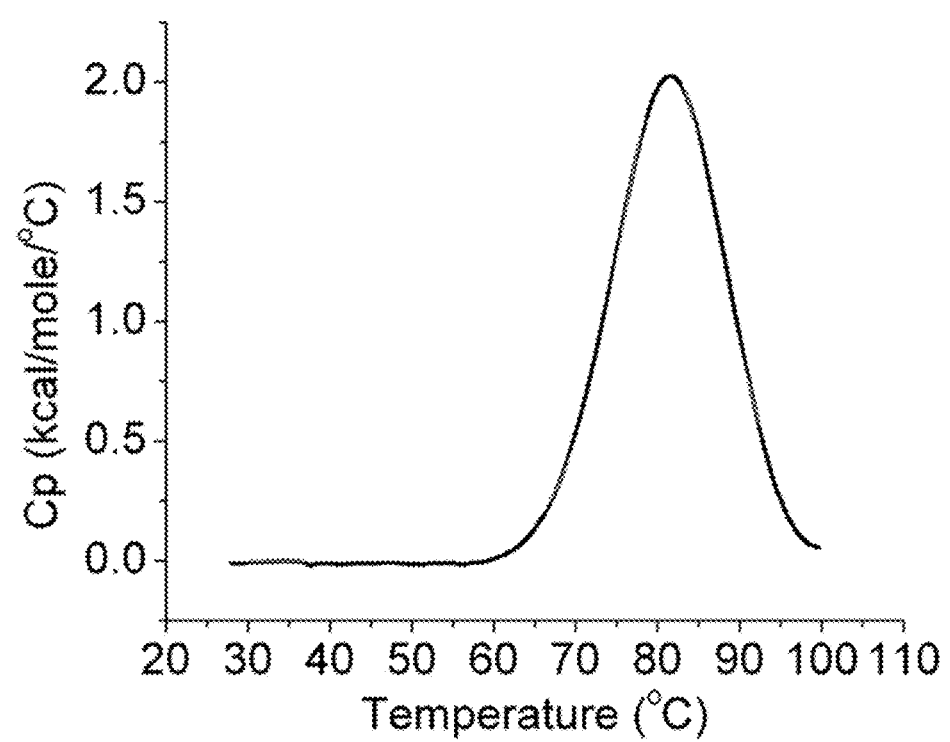
FIG. 4A shows the melting temperature and FIG. 4B shows the reversibility of ABDCon unfolding as measured by DSC in PBS. The normalized, baseline subtracted data for the first scan is shown in FIG. 4A. After the first scan, the sample was cooled to 20° C. and the scan repeated to determine the reversibility of folding. The raw data traces for the first and second scans are overlain in FIG. 4B.
Figure 4B:
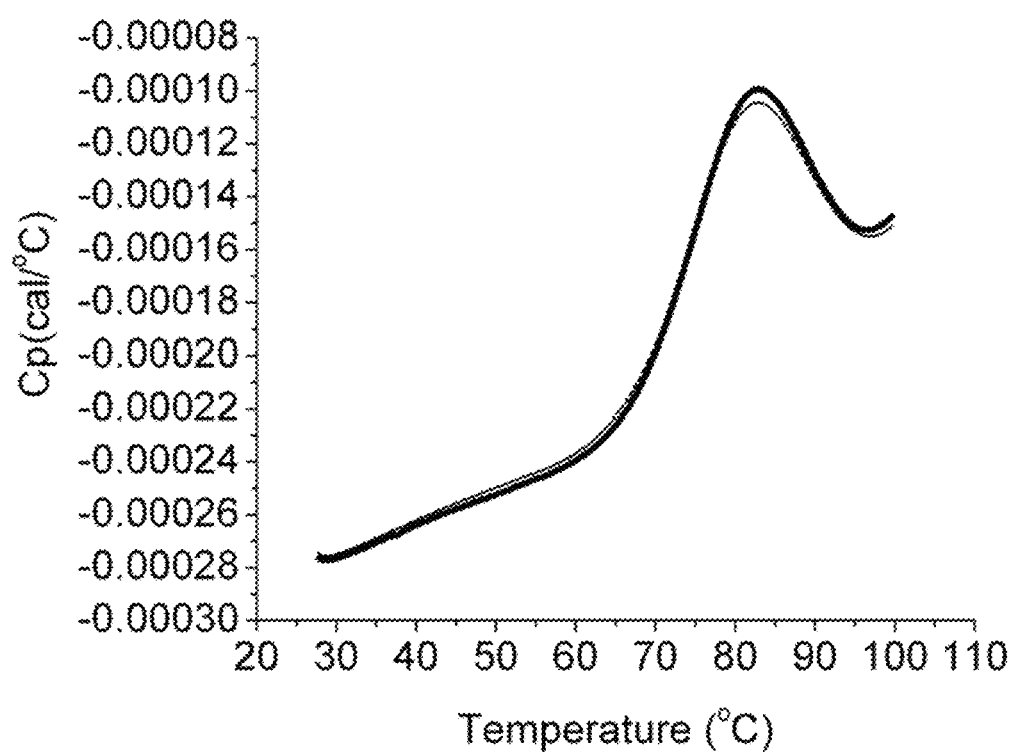

ABDCon was concentrated to 2.175 mg/mL in PBS pH 7.4 and the thermal stability assessed by differential scanning calorimetry (DSC). Stability data was generating by heating 400 µL of the ABDCon solution from 25° C. to 100° C. at a scan rate of 1° C. per minute in a VP-DSC instrument (MicroCal). A second identical scan was completed on the sample in order to assess the reversibility of thermal folding/unfolding. Data was fit to a 2-state unfolding model in order to calculate the melting temperature. FIG. 4A and FIG. 4B shows that ABDCon has a high thermal stability of 81.5° C. in PBS and that folding is fully reversible.

ABDCon Binding to Albumin

The kinetics of ABDCon binding to human serum albumin and mouse serum albumin were measured on a ProteOn™ XPR-36 Protein Interaction Array System (Bio-Rad) using GLC sensor chips. Human (SEQ ID NO: 36), Rhesus (SEQ ID NO: 37), and murine (SEQ ID NO: 38) serum albumins were purchased from Sigma (Catalogue # A4327 for human, #A3559 for murine, and #A4297 for rhesus) and resuspended in PBS at different concentrations. Each serum albumin was directly immobilized on a ligand channel in the vertical orientation of a GLC chip via standard amine coupling at 2.1 µg/mL at pH 5.0 to obtain surfaces with ligand densities of 500-1000 resonance units. Binding of recombinant ABDCon was tested by flowing five different concentrations (e.g. 1 µM diluted in a 3-fold concentration series) as analytes simultaneously in the horizontal orientation over the immobilized serum albumin surfaces. The dissociation phases for all concentrations were monitored for two hours at a flow rate of 100 µL/min using PBST (PBS, 0.005% Tween20) as running buffer. A sixth sample (buffer only) was injected to monitor the baseline stability. The surfaces were regenerated using 1 short pulse (18 µL) of 0.8% phosphoric acid.

TABLE 2

| Albumin | $k_{on}$ (1/Ms) | $k_{off}$ (1/s) | $K_D$ (M) |
| --- | --- | --- | --- |
| Human | 4.04E+05 | 3.02E−05 | 7.48E−11 |
| Mouse | 2.41E+05 | 7.76E−04 | 3.22E−09 |
| Rhesus | 1.13E+06 | 6.78E−05 | 6.01E−11 |

The raw response data were first processed by subtracting the buffer only responses and the non-specific binding between the analytes and the chip. Processed data of all five concentrations were globally fit to a 1:1 simple langmuir binding model for each ligand surface. Table 2 describes the binding kinetics determined for each species of albumin.

Serum Half-Life of ABDCon Fusion in Mice

Figure 5:
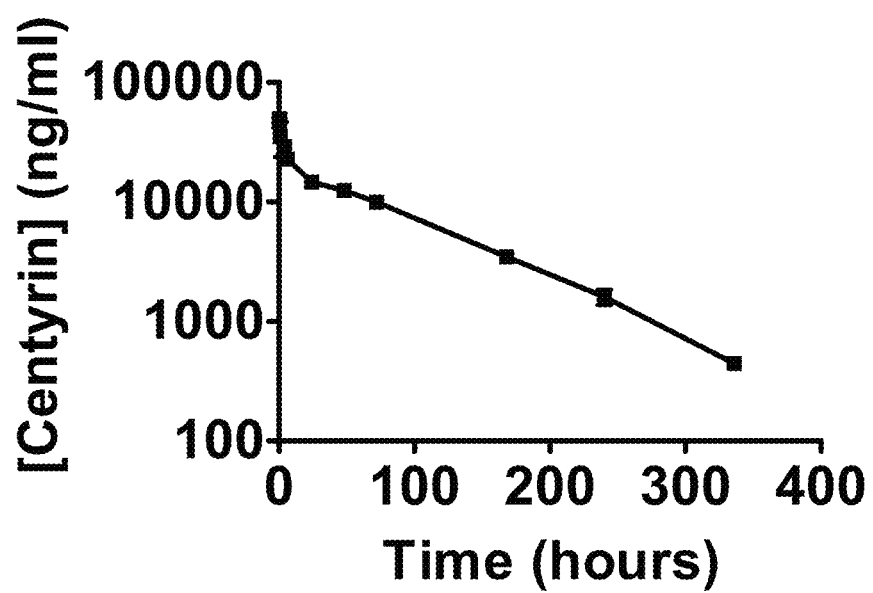
FIG. 5 shows the pharmacokinetics of a Tencon25-ABDCon fusion protein in mice when dosed at 2 mg/kg intravenously.
Figure 6:
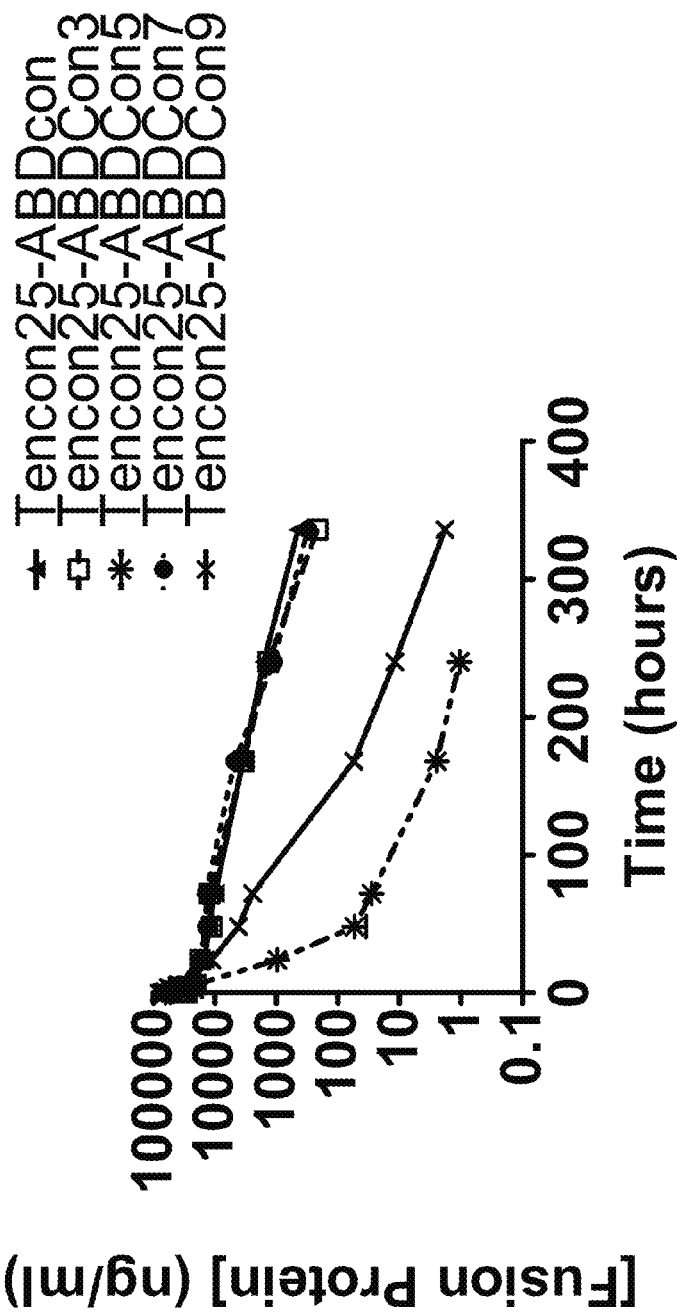
FIG. 6 shows the pharmacokinetics of a Tencon25 (residues 1-90 of SEQ ID NO: 39) molecule fused to ABDCon (SEQ ID NO: 21), ABDCon3 (SEQ ID NO: 26), ABDcon5 (SEQ ID NO: 28), ABDCon7 (SEQ ID NO: 30) and ABDCon9 (SEQ ID NO: 32) in mice when dosed at 2 mg/kg intravenously.

The ability of ABDCon to extend the serum half-life of a fusion protein was evaluated by producing a synthetic gene encoding a fusion of ABDCon to the c-terminus of Tencon25. Tencon25 is a protein scaffold based on a consensus sequence of a fibronectin type III (FN3) repeat protein having a sequence shown in residues 1-90 of SEQ ID NO: 39, and described in US2011/0274623A1. Tencon25 and ABDCon protein domains were fused by a $(G_4S)_2$ peptide linker (SEQ ID NO: 40). The resulting fusion protein has a polypeptide sequence shown in SEQ ID NO: 39. A polyhistidine tag was incorporated at the C-terminus for purification purposes. Sixty nine BALB/c female mice were split into 3 groups (N=3 group 1 non-treated control, and N=33 groups 2-3). Mice were treated with a single intravenous dose of the Tencon25-ABDCon fusion protein at 2 mg/kg. The dosing was based upon the weight of the animals on the day of administration. The mice were euthanized at the following time points after the injection: 10 min, 30 min, 1, 4, 6, hours, and 1, 2, 3, 7, 10, 14 days. Blood samples were taken from each animal via cardiac puncture. The blood samples were allowed to clot at room temperature for 30 minutes, but no longer than 1 hour. The blood samples were then centrifuged at approximately 3,500 rpm for 15 minutes. Serum samples were analyzed using a homogenous sandwich ELISA on the Mesoscale Discovery platform. Streptavidin-Gold plates (Mesoscale Discovery) were blocked for 1 hour with Superblock (TBS) Tween-20 (Thermo). Polyclonal anti-Tencon25 antibody was used for both capture (biotinylated) and detection (labeled with MSD Sulfo-Tag (Mesoscale Discovery)) at 0.625 µg/ml. The antigen and antibodies were added to the plates, which were incubated for 2 hours with vigorous shaking at RT. Plates were washed with TBS-T (Sigma) and MSD Read Buffer with Surfactant (Mesoscale Discovery) was added. The plates were read using the MSD Sector Imager 6000. Data was analyzed using GraphPad Prism. Previous studies have shown that a similar, unfused Tencon molecule is cleared from the bloodstream quickly with a serum half-life of approximately 20 minutes in mice. Fusion of Tencon25 to ABDCon extends the serum half-life to over 60 hours (FIG. 5).

Example 3. Engineering of ABDCon for Varying Affinity to Serum Albumin

The affinity of binding to serum albumin can dictate not only the serum half-life of a therapeutic protein but also the ability of that molecule to bind and neutralize its target. For example, a molecule that binds serum albumin too weakly will have short serum half-life due to renal filtering while not bound to albumin (Hopp et al., Protein Eng Des Sel 23:827-834, 2010). On the contrary, a molecule that binds to albumin too tightly will not be released from albumin at the preferred site of action and thus may be unable to neutralize the desired target in some cases. It is therefore preferable to achieve half-life extension via albumin binding in a way in which the albumin interaction is only tight enough to give the desired serum half-life. As the ABDCon sequence described herein binds to human serum albumin with an affinity of 75 pM and an off-rate of $3.02 \times 10^{-5}$ 1/s (under experimental conditions described herein), molecules fused to ABDCon will be largely bound to albumin once administered to an animal or patient. For some targets and fusions, it may be desirable to be bound less tightly to serum albumin. Ten mutant versions of ABDCon were designed to lower the binding affinity of ABDCon for albumin. Table 3 summarizes these mutants:

TABLE 3

| Construct | Mutation* | SEQ ID NO: | Rationale |
| --- | --- | --- | --- |
| ABDCon2 | Y21A | 25 | Disrupt aromatic stacking with albumin residues F309 and F326 |

TABLE 3-continued

| Construct | Mutation* | SEQ ID NO: | Rationale |
|---|---|---|---|
| ABDCon3 | Y21K | 26 | Disrupt aromatic stacking with albumin residues F309 and F326. Insert steric clash |
| ABDCon4 | Y22A | 27 | Decrease hydrophobic contacts |
| ABDCon5 | Y22S | 28 | Decrease hydrophobic contacts |
| ABDCon6 | Y22V | 29 | Decrease hydrophobic contacts slightly |
| ABDCon7 | E41Q | 30 | Remove charge to disrupt salt-bridge |
| ABDCon8 | K30D | 31 | Alter charge to disrupt salt-bridge |
| ABDCon9 | T31A | 32 | Remove intermolecular hydrogen bond |
| ABDCon10 | A37V | 33 | Introduce steric clash |
| ABDCon11 | A37Y | 34 | Introduce steric clash |

*Amino acid numbering according to SEQ ID NO: 21

ABDCon mutants were selected by examining the crystal structure of the GA module (protein G-related albumin binding module) bound to human serum albumin (PDB code 1TFO) (Lejon et al., Acta Crystallogr Sect F Struct Biol Cryst Commun 64:64-69, 2008) and making the assumption that ABDCon binds to albumin in a manner very similar to GA. Mutants were designed to decrease the affinity of ABDCon for albumin by disrupting hydrophobic contacts, introducing steric clashing, disrupting salt bridges, and disrupting hydrogen bonding (Table 3). Changes introduced were designed to decrease binding affinity without changing the binding surface so dramatically that binding was abolished. Each mutant was expressed and purified from *E. coli* as described for ABDCon. Mutant ABDCon11 was found to be insoluble and thus excluded from further analysis. The affinities of each variant for human, mouse, and rhesus serum albumin were determined by surface plasma resonance and shown in Table 4. In addition to the positions listed in Table 3, residues L25, E33, G34, L38, I42, and A45 may be mutated to increase or decrease the affinity of ABDCon for albumin as they are predicted to form direct contacts with albumin.

TABLE 4

| Variant | $K_D$ Human (nM) | $K_D$ Mouse (nM) | $K_D$ Rhesus (nM) |
|---|---|---|---|
| ABDCon2 | 6.1 | ND | 17.5 |
| ABDCon3 | 1 | 103 | 5.1 |
| ABDCon4 | 13.6 | 571 | 43.7 |
| ABDCon5 | 54.8 | 1650 | 104 |
| ABDCon6 | 2.7 | 190 | 8.4 |
| ABDCon7 | 0.4 | 20.6 | 0.5 |
| ABDCon8 | 43 | 1001.7 | 65 |
| ABDCon9 | 860 | 550.8 | 206 |
| ABDCon10 | 0.8 | 37.8 | 1.3 |

Example 4. Serum Half-Life of ABDCon Variant Fusion Proteins

Tencon25 (amino acids 1-90 of SEQ ID NO: 39) was fused to ABDCon variants 3, 5, 7, and 9 (Table 3) in order to assess the correlation between ABDCon affinity for albumin with half-life extension. These molecules were dosed into mice at 2 mg/kg as described above in previous studies and analyzed using identical methods as described for the Tencon25-ABDCon fusions. A summary of the PK parameters obtained for these molecules is shown in Table 5 and FIG. 6. Here it is demonstrated that the rate of clearance decreases as affinity for albumin is increased until reaching an affinity of 103 nM at which point, no large differences in PK parameters are obtained. The data in Table 5 demonstrate the ability to tune properties such as half-life, rate of clearance, and total exposure (AUC) by varying the affinity of the ABDCon molecule for albumin.

TABLE 5

| Construct | $K_D$ (nM) | T (½) (hours) | Volume of Distribution (mL/kg) | Clearance (mL/hr/kg) | AUC (hour * ng/ml) |
|---|---|---|---|---|---|
| Tencon25-ABDCon | 1.86 | 60.42 | 83.2873 | 0.9555 | 2054332 |
| Tencon25-ABDCon3 | 103 | 45.8355 | 60.645 | 0.915 | 2166461 |
| Tencon25-ABDCon5 | 1650 | 32.8715 | 223.86 | 4.72 | 423635 |
| Tencon25-ABDCon7 | 20.6 | 46.7499 | 49.915 | 0.74 | 2681641 |
| Tencon25-ABDCon9 | 550.8 | 34.1956 | 81.87 | 1.66 | 1205061 |

TABLE 6

| SEQ ID | Sequence |
|---|---|
| 13 | LKEAKEKAVEELKENGITSEKYIDQINKAKTVEGVNALKDEIIKA |
| 14 | LKEAKEKAVEELKNNGITSEKYIDQINKAKTVEGVNALKDEIIKA |
| 17 | LKEAKEKAVEELKNNGITSEKYIEQINKAKTVEGVNALKDEIIKA |
| 20 | LKEAKEKAIEELKNNGITSEKYIEQINKAKTVEGVNALKDEIIKS |
| 7 | LKDAKEKAIEAIRKEGVKSKLYEDLINKAKTIDGVNALRDQIIEA |
| 1 | LAEAKVLANRELDKYGVS-DYYKNLINNAKTVEGVKALIDEILAA |
| 2 | LSEAKEMAIRELDAQGVS-DFYKNKINNAKTVEGVVALKDLILNS |
| 3 | LDQAKQAALKEFDRYGVS-NYYKNLINKAKTVEGIMELQAQVV-- |
| 12 | LAEAKKVAHEEFTKAGITGKIFHDAIDAAKTVEGLKAYVAETLAA |
| 15 | LAEAKKVAHEEFTKAGITGKIFHDAIDAAKTVEGLQAYVAETLAA |
| 18 | LAEAKNVAHAEFTKAGITGKIFHDAIDAAKTVEGLQAYVAETLAA |
| 19 | LAEAKKAAHEEFTKAGITGKIFHDAIDAAKTVEGLQAYVAETLKA |
| 4 | LAQAKEAAIKELKQYGIG-DYYIKLINNAKTVEGVESLKNEILKA |
| 5 | LLKAKEAAINELKQYGIS-DYYVTLINKAKTVEGVNALKAEILSA |
| 16 | LKNAKEDAIAELKKAGITSDFYFNAINKAKTVEEVNALKNEILKA |
| 10 | LKNAKEDAIKELKEAGISSDIYFDAINKAKTVEGVEALKNEILKA |
| 11 | LKNAKEDAIKELKEAGITSDIYFDAINKAKTIEGVEALKNEILKA |

TABLE 6 -continued

| SEQ ID | Sequence |
|---|---|
| 6 | LKNAKEDAIKELKEAGIKSQFFFNLINNAKTVEGVESLKNEILKA |
| 9 | LKNAKEAAIKELKEAGITAEYLFNLINKAKTVEGVESLKNEILKA |
| 8 | LKNAKEEAIKELKEAGITSDLYFSLINKAKTVEGVEALKNEILKA |
| 21 | LKEAKEKAIEELKKAGITSDYYFDLINKAKTVEGVNALKDEILKA |

Example 5. Stabilization of Albumin Binding Domains

Figure 7A:
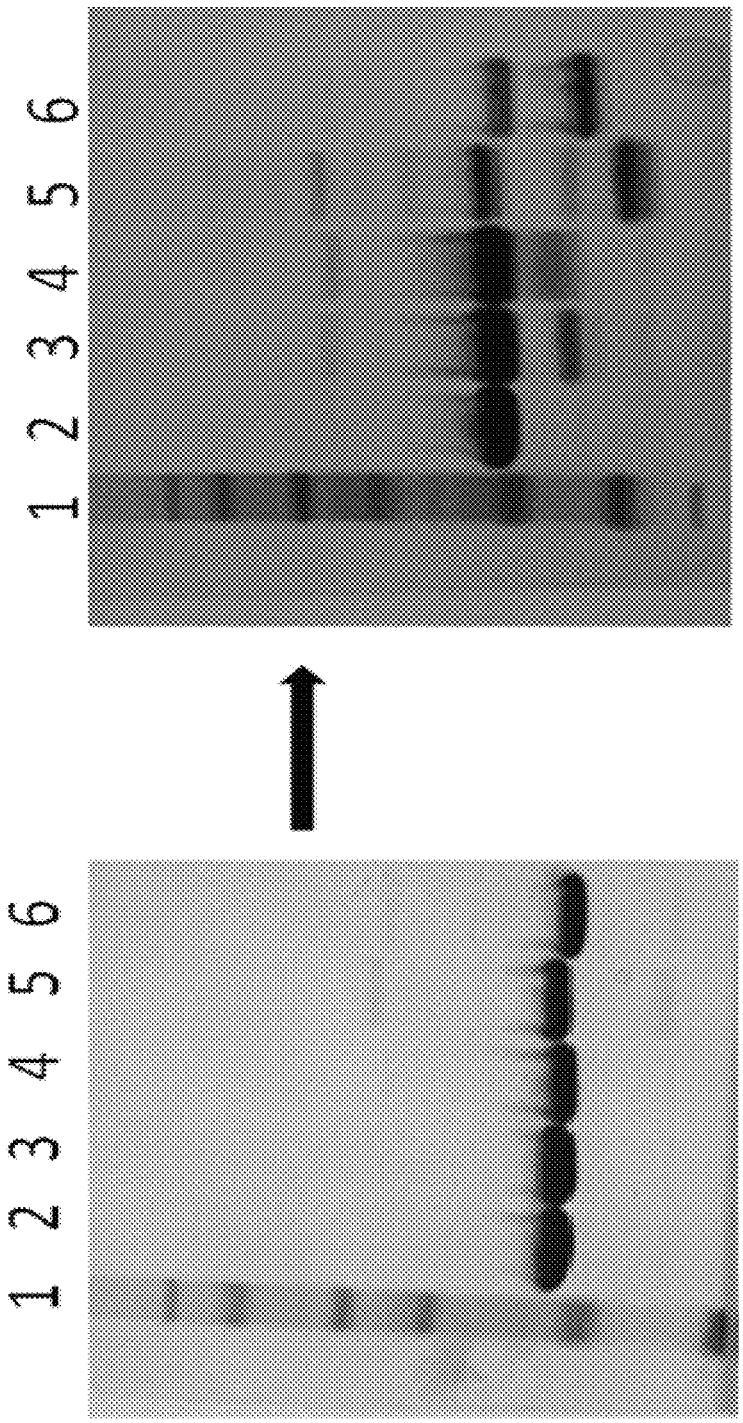
FIG. 7A shows stability of several FN3 domainABDCon fusion proteins when incubated at 37° C. for 0 days (left panel) or 28 days (right panel) in PBS as assessed on SDS-PAGE. Left panel lines from left to right: Lane 1:molecular weight marker, Lane 2: Tencon-ABDCon, Lane 3: Tencon-ABDCon, Lane 4:Tencon25-ABDCon, Lane 5: 83-ABDCon, Lane 6: 71-ABDCon fusion proteins. Right panel lanes: Lane 1: molecular weight marker, Lane 2: Tencon-ABDCon4C, Lane 3: Tencon-ABDCon, Lane 4:Tencon25-ABDCon, Lane 5:83-ABDCon, Lane 6: 71-ABDCon fusion proteins.

Studies were completed to determine the stability of ABDCon (SEQ ID NO: 21) when produced as fusion proteins with various fibronectin type III (FN3) domains (see, for example, U.S. Pat. Publ. No. US2010/0216708). The FN3 domain-ABDCon fusion proteins were generated using standard cloning techniques. The amino acid sequence of one of the fusion proteins, Tencon-ABDCon is shown in SEQ ID NO: 41. Other FN3 domain-ABDCon fusion proteins made were Tencon25-ABDCon, 83-ABDCon and 71-ABDCon. These proteins were produced with c-terminal poly histidine tags and purified by a combination of nickel affinity and size exclusion chromatography using standard methods. Each purified molecule was incubated in PBS pH 7.4 at 37° C. for 28 days before analysis by SDS-PAGE and Mass Spectrometry. FIG. 7A demonstrates that each FN3 domain-ABDCon fusion protein was found to be degraded during this incubation as evidenced by the appearance of low molecular weight bands on the SDS-PAGE gel. Mass Spectrometry analysis confirmed that the main degradation pattern was clipping of these molecules at residues L1, K2, and E3 of the ABDCon sequence (SEQ ID NO: 21). In addition, it was observed that the native *Streptococcus* protein G ABD (SEQ ID NO: 1) fused to a FN3 domain displayed a similar degradation pattern with clipping at residue L1 when incubated at 4° C. for 6-8 months (Data not shown). Finally, several purified lots of native ABD (SEQ ID NO:1) and ABDCon (SEQ ID NO: 21) were observed to be inactive and undetectable in solution by SDS-PAGE once stored for several months at 4° C., indicative of severe degradation.

The above observations suggested that the N-terminal alpha helix of the ABDCon and native ABD structures as used for serum half-life extension are unstable. This lack of stability for such fusion proteins is undesirable as it potentially limits the shelf-life of such molecules for research as well as therapeutic applications. As such, a strategy was developed to improve the stability of these molecules. Analysis of the three dimensional structures of albumin binding domains deposited in the Protein Data Bank shows that the amino acid sequence TIDQWL (SEQ ID NO: 42) found N-terminal to the start of the native ABD (SEQ ID NO: 1) is structurally ordered as part of the first alpha helix of this molecule in several crystal structures (e.g. PDB 2VDB, *Acta Cryst* 2008 F64, 64-69). This is in contrast to the original NMR structure of the ABD which showed this region to be disordered in solution (PDB 1GAB, Johansson et al., J. Mol. Biol. 266: 859-865, 1997). Thus, it was hypothesized that extending this first alpha helix of the ABD and ABDCon sequences could impart greater stability to this region as extending alpha helices can impart greater stability to such a helix (Su et al., Biochemistry 33:15501-15510, 1994).

Figure 7B:
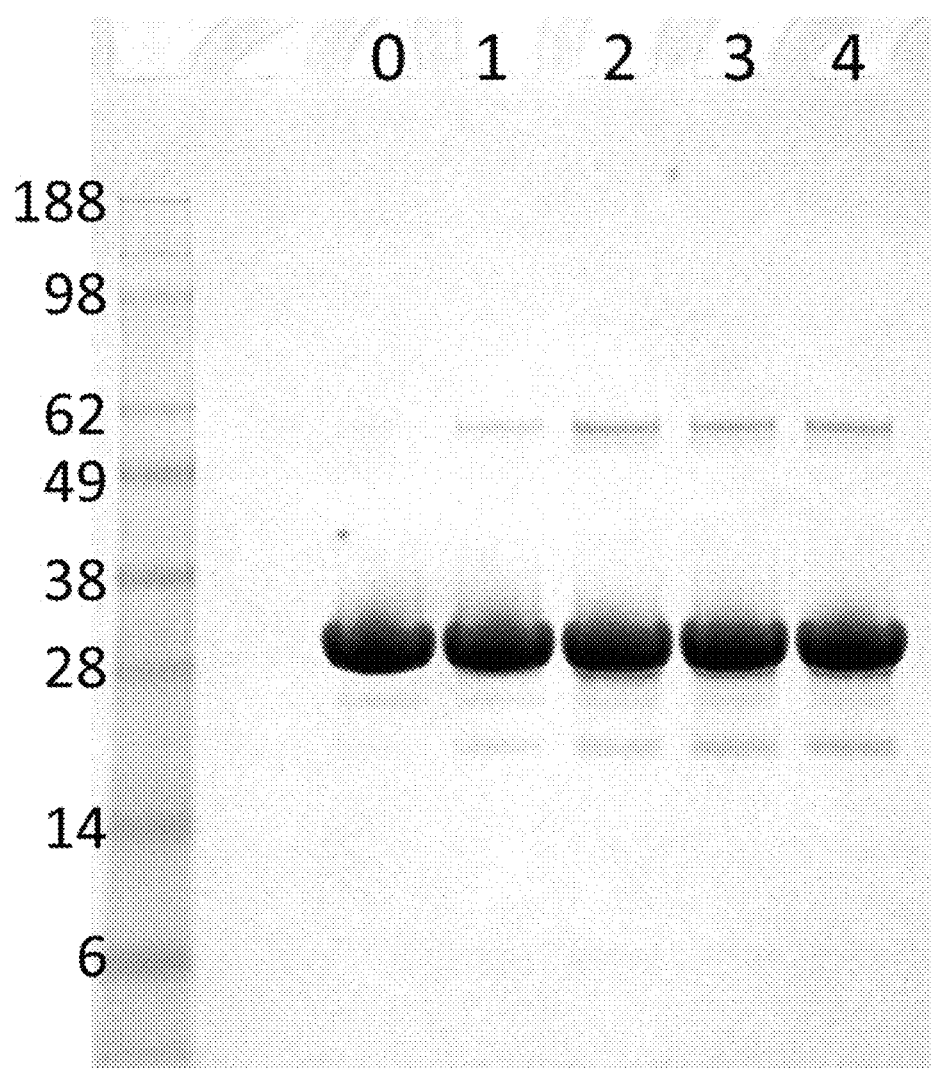
FIG. 7B shows stability of FN3 domain-ABDCon12 having an extended N-terminal helix after 0, 1, 2, 3 or 4 week incubation (as indicated above the lanes) at 37° C. in PBS.

A multiple sequence alignment of the natural albumin binding domains presented in Table 1 revealed no clear consensus sequence for these N-terminal residues. However one peptide sequence, TIDEWL (SEQ ID NO: 43), is present N-terminal to 5 of these protein domains. Thus, a new ABDCon construct, ABDCon12 (SEQ ID NO: 44), was generated by adding the TIDEWL sequence to the N-terminus of ABDCon. This protein was expressed with an N-terminal poly histidine tag and purified to homogeneity using standard methods for nickel affinity chromatography and size exclusion chromatography. Purified ABDCon12 was incubated at 37° C. in PBS for 28 days and stability assessed by SDS-PAGE and mass spectrometry. SDS-PAGE showed a slightly faster migration pattern after day 14 indicative of degradation. Total mass analysis however demonstrates that this degradation is occurring exclusively in the polyhistidine tag and not in the ABDCon12 sequence, indicating that the TIDEWL sequence improved the stability of ABDCon. Further proof of stability was demonstrated in the stability of a generated FN3 domain-ABDCon12 fusion protein (FIG. 7B) which showed significantly less degradation products compared to the original FN3 domain-ABDCon molecules (FIG. 7A) when incubated at 37° C. in PBS for 28 days.

The melting temperature of ABDCon12 was determined by differential scanning calorimetry using the procedures outlined in Example 2 above in order to investigate the mechanism of stabilization for this molecule. A melting temperature of 90.9° C. was obtained in PBS, a 9.4° increase compared to the original ABDcon molecule, suggesting that the decrease in proteolysis/degradation observed for ABDCon12 and ABDCon12 fusion proteins is a result of increased conformational stability afforded by the extension of the N-terminal alpha helix.

```
SEQ ID NO 41: Tencon-ABDCon
MLPAPKNLVVSEVTEDSLRLSWTAPDAAFDSFLIQYQESEKVGEAINLTV

PGSERSYDLTGLKPGTEYTVSIYGVKGGHRSNPLSAEFTTGGGGSGGGGS

LKEAKEKAIEELKKAGITSDYYFDLINKAKTVEGVNALKDEILKAGGHHH

HHH

SEQ ID NO: 42: N-terminal sequence of Strep G. ABD
TIDQWL

SEQ ID NO: 43: N-terminal sequence appended to
ABDCon
TIDEWL

SEQ ID NO: 44: ABDCon12
TIDEWLLKEAKEKAIEELKKAGITSDYYFDLINKAKTVEGVNALKDEIL

KA
```

Example 6. Characterization of ABDCon12

The affinity of purified ABDCon12 binding to human and murine albumin was determined by surface plasmon resonance using the same methods as described above in Example 2. Dissociation constants of 0.7 nM and 8.2 nM were obtained for ABDCon12 binding to human and murine albumin, respectively. The ability of ABDCon12 to extend the serum half-life of a fusion molecule was demonstrated by fusing ABDCon12 to the C-terminus of an FN3 domain specifically binding an antigen. This molecule was administered to mice by IP injection at 2 mg/kg and analyzed as described above in Example 4. A terminal half-life of 55 hours was measured for the FN3 domain-ABDCon12 fusion protein.

Example 7: Stabilizing Albumin Binding Domains

Based on sequence analysis of naturally occurring albumin binding domains, it is anticipated that other sequences added to the N-terminus of albumin binding domains may make them more stable. For example, a number of different sequences are found N-terminal to these natural albumin binding domains such as but not limited to APAVDV (SEQ ID NO: 45), IAKEKA (SEQ ID NO: 46), TIDQWL (SEQ ID NO: 42), VPAADV (SEQ ID NO: 47), TVKSIE (SEQ ID NO: 48), TPAVDA (SEQ ID NO: 49), TLKSIK (SEQ ID NO: 50), WEKAAA (SEQ ID NO: 51), AVDANS (SEQ ID NO: 52), QLAAEA (SEQ ID NO: 53), ALKAAA (SEQ ID NO: 54), EKLAAA (SEQ ID NO: 55). Addition of these sequences to albumin binding domains might increase stability if these sequences produce longer alpha helices. In addition, non-natural peptides that increase alpha helix length or stability are predicted to stabilize albumin binding domains as well.

Variants with additional N-terminal sequences can be generated using standard techniques and their properties tested as described supra.

It will be clear that the invention can be practiced otherwise than as particularly described in the foregoing description and examples. Numerous modifications and variations of the present invention are possible in light of the above teachings and, therefore, are within the scope of the appended claims.

What is claimed:

1. An isolated polynucleotide encoding an albumin binding domain comprising an amino acid sequence selected from the group consisting of SEQ ID NOs: 21-34.

2. The nucleotide of claim 1, further comprising a nucleotide encoding an extension of 5 amino acids at the N-terminus of the albumin binding domain.

3. The nucleotide of claim 2, wherein the nucleotide encoding the extension encodes an extension selected from the amino acid sequences of SEQ ID NOs: 42, 43 or 45-55.

4. The nucleotide of claim 3, wherein the nucleotide encoding the extension encodes the amino acid sequence of SEQ ID NO:43.

5. The nucleotide of claim 3, wherein the nucleotide encoding the extension encodes the amino acid sequence of SEQ ID NO:44.

6. An isolated vector comprising the isolated polynucleotide of any one of claims 1-5.

7. A host cell comprising the isolated vector of claim 6.

8. A method of producing an albumin binding domain, comprising expressing the albumin binding domain of claim 1 in a host cell and recovering the albumin binding domain from the cell.

* * * * *